(12) United States Patent
Babiel et al.

(10) Patent No.: US 7,920,971 B2
(45) Date of Patent: Apr. 5, 2011

(54) QUANTIFICATION SCHEMES FOR QUANTIFYING NUCLEIC ACIDS

(75) Inventors: Reiner Babiel, Seehausen (DE); Norbert Franken, Starnberg (DE); Hermann Leying, Bichl (DE); Judith Pinsl-Ober, Tutzing (DE); Thomas Vess, El Sobrante, CA (US); Guenter Ziegler, Polling (DE)

(73) Assignee: Roche Molecular Systems, Inc., Pleasanton, CA (US)

( * ) Notice: Subject to any disclaimer, the term of this patent is extended or adjusted under 35 U.S.C. 154(b) by 1423 days.

(21) Appl. No.: 10/571,958

(22) PCT Filed: Sep. 24, 2004

(86) PCT No.: PCT/EP2004/010712
§ 371 (c)(1),
(2), (4) Date: Mar. 13, 2006

(87) PCT Pub. No.: WO2005/030990
PCT Pub. Date: Apr. 7, 2005

(65) Prior Publication Data
US 2006/0292571 A1    Dec. 28, 2006

(51) Int. Cl.
G01N 33/48    (2006.01)
(52) U.S. Cl. .................................................... 702/19
(58) Field of Classification Search .................. 702/19
See application file for complete search history.

(56) References Cited

U.S. PATENT DOCUMENTS

| | | | | |
|---|---|---|---|---|
| 4,683,195 | A | 7/1987 | Mullis et al. | 435/6 |
| 4,683,202 | A | 7/1987 | Mullis et al. | 435/91 |
| 5,118,801 | A | 6/1992 | Lizardi et al. | 536/27 |
| 5,389,512 | A | 2/1995 | Kwok et al. | 435/5 |
| 5,476,774 | A | 12/1995 | Wang et al. | 435/91.2 |
| 6,303,305 | B1 | 10/2001 | Wittwer et al. | 435/6 |
| 6,503,720 | B2 | 1/2003 | Wittwer et al. | 435/6 |
| 2002/0028452 | A1 | 3/2002 | Wittwer et al. | 435/6 |
| 2002/0031768 | A1 | 3/2002 | McMillan et al. | 435/6 |
| 2002/0034745 | A1 | 3/2002 | McMillan et al. | 435/6 |
| 2002/0034746 | A1 | 3/2002 | McMillan et al. | 435/6 |
| 2002/0058262 | A1 | 5/2002 | Sagner et al. | 435/6 |
| 2002/0058282 | A1 | 5/2002 | McMillan et al. | 435/6 |

FOREIGN PATENT DOCUMENTS

| | | |
|---|---|---|
| EP | 0 953 379 A11 | 11/1999 |
| EP | 0 953 837 A1 | 11/1999 |
| EP | 0 955 097 A1 | 11/1999 |
| EP | 1 041 158 B1 | 10/2000 |
| EP | 1 138 783 A3 | 2/2001 |
| EP | 1 138 784 A3 | 2/2001 |
| JP | 2001314194 A | 11/2001 |
| JP | 2001314195 A | 11/2001 |
| WO | WO 97/46707 | 12/1997 |
| WO | WO 97/46712 | 12/1997 |
| WO | WO 97/46714 | 12/1997 |
| WO | WO 2005/030990 A1 | 4/2005 |

OTHER PUBLICATIONS

Bernard, P., et al., 1998, "Integrated Amplification and Detection of the C677T Point Mutation in the Methylenetetrahydrofolate Reductase Gene by Fluorescence Resonance Energy transfer and Prove Melting Curves", *Analytical Biochemistry*, 255:101-107.
PCT/EP2004/010712, Sep. 24, 2004, PCT Search Report.
Bièche, I., et al. 1999, "Quantitation of *MYC* Gene Expression in Sporadic Breast Tumors with a Real-Time Reverse Transcription-PCR Assay", *Cancer Research*, 59:2759-2765.
Gibson, U., et al., 1996, "A Novel Method for Real Time quantitative RT-PCR", *Genome Research*, 6:995-1001.
Higuchi, R., et al., 1993, "Kinetic PCR Analysis: Real-time Monitoring of DNA Amplification Reactions", *Bio/Technology*, 11:1026-1030.
"Relative Quantification, LightCycler—Roche Applied Science Technical Note No. LC 13/2001".
Siebert, P., 1998, "Quantitative RT-PCR", *Methods In Molecular Medicine—Molecular Diagnosis of Infectious Diseases*, 55-79.
Willems, H., et al., 1984, "Polymerase Chain Reaction", *Ullmann's Encyclopedia of Industrial Chemistry*, 25:125-159.
Wittwer, C., et al., 1997, "The LightCycler™: A Microvolume Multisample Fluorimeter with Rapid Temperature Control", *BioTechniques*, 22:176-278.
Zimmermann, K., et al., 1996, "Technical Aspects of Quantitative Competitive PCR", *BioTechniques*, 21(2):268-278.

*Primary Examiner* — Jerry Lin
(74) *Attorney, Agent, or Firm* — Charles M. Doyle; David J. Chang

(57) ABSTRACT

Method and apparatus, including computer program products, implement techniques for quantifying a target nucleic acid (target) in a test sample. The techniques include providing a target and a defined initial amount of an internal control nucleic acid (control) different from the target; amplifying the target and control in a common amplification process; measuring a quantity indicating the amount of amplification product for the target and for the control in relation to a parameter representing the progress of the amplification; determining a characteristic value of the progress parameter for the target based on measurement results related to the amount of target amplification product; possibly determining a characteristic value of the progress parameter for the control based on measurement results related to the amount of control amplification product; and quantifying the original amount of target according to a predefined or selected quantification scheme using at least the characteristic value for the target.

29 Claims, 21 Drawing Sheets

$$\{ (T_{0i}, \Delta n_i); i=1,\ldots,S; nQ_i = \checkmark \} \quad \text{(A-7)}$$

$T_{0i} = f \times Q_0 \times (1 + \varepsilon)^x \; ; \; x \triangleq \Delta n_i$

FIT TO CALIBRATION FORMULA (A-8)

$\log(T_{0i}) = (ax^2 + bx + c) + \log(Q_0)$

**Calibration Constants a, b, c,
Amplification Efficiency $\varepsilon$,
Proportionality Constant f** (A-9)

Fig. 1b

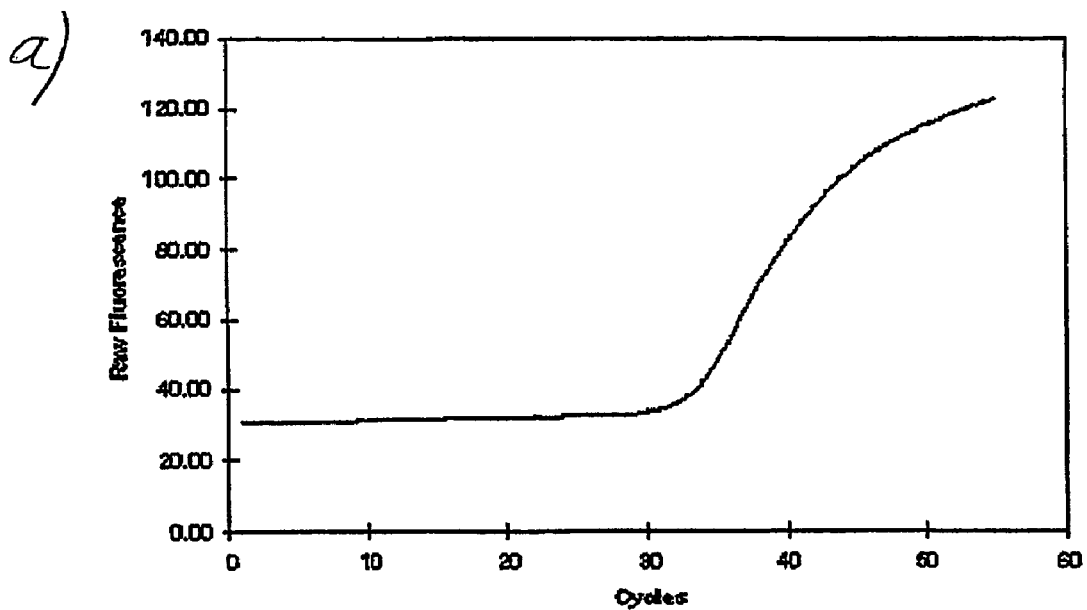
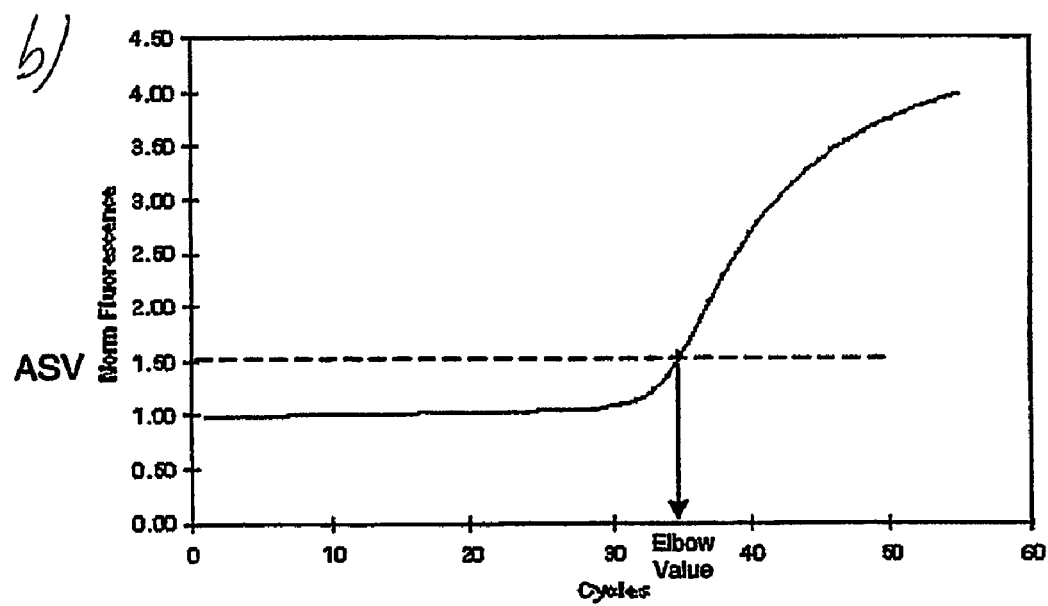
Fig. 2

B) CALIBRATION ON BASIS OF STANDARD FOR HIGH TARGET CONCENTRATIONS

B1)

$$\left\{ (T_{0i}, nT_i); i=1,\ldots,S \right\} \quad \text{(B1-1)}$$

$$T_{0i} = T_i(nT_i) \times (1 + \varepsilon)^{-y} \,;\, y \triangleq nT_i$$

FIT TO CALIBRATION FORMULA (B1-2)

$$\log(T_{0i}) = Ax^2 + Bx + C$$

Calibration Constants A, B, C (B1-3)
Amplification Efficiency $\varepsilon$

B2)

$(T_{0j}, nT_j)$ for Sample j which has an Elbow Value $nT_j$ corresponding approximately to a predefined reference value $nT_{ref}$, e.g. $nT_{ref} = 20$; $T_{ref} := T_{0j}, nT_{ref} := nT_j$ (B2)

possibly to be used with theoretical
Amplification Efficiency $\varepsilon$ ( e.g. $\varepsilon = 1$)
or with Amplification Efficiency obtained from
the calibration, e.g. calibration A) or calibration B1)

Fig. 9

C) STANDARD QUANTIFICATION $$\left\{ \begin{array}{l} \text{Sample}_i[T_{0i}, Q_0]; \; i=1,\ldots,S; \\ S \geq 1; \; T_{0i} = ? \end{array} \right\} \quad \text{(C-1)}$$

PCR-AMPLIFICATION WITH MEASUREMENT OF
FLUORESCENSE INTENSITY OVER CYCLES 1 TO P,
CROSSTALK CORRECTION OF THE FLUORESCENCE  (C-2)
SIGNALS VIA MULTICOMPONENT ANYLYSIS $$\left\{ \begin{array}{l} \text{Target Growth Curves } T_i(\text{cycle}_k), \\ \text{Control Growth Curves } Q_i(\text{cycle}_k); \\ k = 1,\ldots,P; \; i=1,\ldots,S \end{array} \right\} \quad \text{(C-3)}$$

PRECHECKS, CORRECTIONS,
DATA NORMALIZATION,
DETERMINATION OF ELBOW VALUES  (C-4)

$$\left\{ \begin{array}{l} \text{Target Elbow Values } nT_i, \\ \text{Control Elbow Values } nQ_i \, ; \; i=1,\ldots,S \end{array} \right\} \quad \text{(C-5)}$$

CALCULATION OF ELBOW DIFFERENCES  (C-6)
$\Delta n_i = nQ_i - nT_i$

Fig. 10a

D) EXCEPTIONAL QUANTIFICATION

D1)

$$\left\{ nT_i, i=1,\ldots,S; \; nQ_i \neq \checkmark \right\} \quad \text{(D1-1)}$$

$T_{oi} = T_i(nT_i) \times (1 + \varepsilon)^{-y}$ ; $y \triangleq nT_i$

CALIBRATION FORMULA (D1-2)

$\log(T_{oi}) = Ax^2 + Bx + C$

CONSTANTS A, B, C FROM CALIBRATION

Initial Titer Values $T_{oi}$ (D1-3)

$$\left\{ nT_i, i=1,\ldots,S; \ nQ_i \neq \checkmark \right\} \quad \text{(D2-1)}$$

$$T_{oi} = T_{ref} \times (1 + \varepsilon)^z \ ; \ z \triangleq nT_{ref} - nT_i$$

(D2-2)

$T_{ref}$, $nT_{ref}$ AND POSSIBLY $\varepsilon$ FROM CALIBRATION

Initial Titer Values $T_{oi}$ (D2-3)

Fig. 11b

COBAS AmpliPrep™ COBAS TaqMan™
48 Tests
CAP—G/CTM HBV Test

P/N:N33701941 90
2—8°C

DOM: 01/09/03
LOT: D09569

FOR DEVELOPMENT USE

Manufactured by Roche Molecular Systems, Inc., Branchburg, NJ USA

Formula : F0

$$T = v \cdot \frac{Q}{r} \cdot 10^{\overline{a}*(ct_{QS}-ct_T)^2 + \overline{b}*(ct_{QS}-ct_T) + \overline{c}}$$

where $\overline{a}, \overline{b}, \overline{c}$ = calibration coefficients
$ct_{QS}$ = elbow value of QS growth curve
$ct_T$ = elbow value of target growth curve
$v$ = volume factor [Assay−Vol.**/ml]
$Q$ = QS concentration [IU / Assay−Vol.**]
$r$ = recovery [default =1]

Formula : Standard $$T = 10^{a*(ct_{QS}-ct_T)^2 + b*(ct_{QS}-ct_T) + c}$$

where $a, b, c$ = calibration coefficients, different from $\overline{a}, \overline{b}, \overline{c}$; specific for chosen QS copy number, recovery and volume factor
$ct_{QS}$ = elbow value of QS growth curve
$ct_T$ = elbow value of target growth curve $$T = T_{ref} \cdot 2^{(ct_{ref}-ct_T)}$$

where $T_{ref}$ = copy number of a high positive control or reference which is found with a $ct_{ref}$ of about 20
$ct_{ref}$ = elbow value for $T_{ref}$
$ct_T$ = elbow value for target

*Formula: F1*

$$T = T_{ref} \cdot (e^{b \cdot \ln 10})^{(ct_{ref}-ct_T)}$$

where $T_{ref}$ = copy number of a high positive control or reference which is found with a $ct_{ref}$ of about 20
$ct_{ref}$ = elbow value for $T_{ref}$
$ct_T$ = elbow value for target
$b$ = calibration coefficient of formula 2

*Formula: F2*

*Fig. 17b*

$afin_{ref}$ = plateau value of QS normalized and drift corrected growth curve

QUANTIFICATION SCHEMES FOR QUANTIFYING NUCLEIC ACIDS

TECHNICAL FIELD

This invention relates to the quantification (quantitation) of nucleic acids.

BACKGROUND

Methods for the quantification (quantitation) of nucleic acids are important in many areas of molecular biology and in particular for molecular diagnostics. At the DNA level such methods are used for example to determine the copy numbers of gene sequences amplified in the genome. Further, methods for the quantification of nucleic acids are used in connection with the determination of mRNA quantities since this is usually a measure for the expression of the respective coding gene.

Among the number of different analytical methods that detect and quantify nucleic acids or nucleic acid sequences, Polymerase Chain Reaction (PCR) has become the most powerful and widespread technology, the principles of which are disclosed in U.S. Pat. Nos. 4,683,195 and 4,683,202 (Mullis et al.). However, a typical PCR reaction by itself and correspondingly a typical reverse-transcriptase PCR (RT-PCR) reaction by itself only yields qualitative data, since, after a phase of exponential or progressive amplification, the amount of amplified nucleic acid reaches a plateau, such that the amount of generated reaction product is not proportional to the initial concentration of the target nucleic acid or target nucleic acid sequence, in particular template DNA. However, an end point analysis reveals the presence or absence of a respective starting nucleic acid. This information is, for certain applications, in particular clinical applications, of high value. For other applications including clinical applications, a quantitative measurement is needed, for example to make a proper diagnosis with respect to certain diseases. For example, precise quantitative measurements are needed to diagnose certain infectious diseases, cancers and autoimmune diseases. It may be useful therapeutically to assess the response of a disease to treatment and make prognoses for recovery. Precise quantitative measurement may also help detect false positives, which can occur if there is any contamination of a sample.

SUMMARY

The invention provides a method for quantification of at least one target nucleic acid in a test sample or in a plurality of test samples. In general, in one aspect, the method comprises: providing at least one target nucleic acid together with at least one internal control in a common test sample, the internal control comprising a defined initial amount of a control nucleic acid different from the target nucleic acid; amplifying the target nucleic acid and the control nucleic acid within the test sample in a common nucleic add amplification process; directly or indirectly measuring the amount of amplification product or a quantity indicating the amount of amplification product for the target nucleic add and the control nucleic acid during the amplification in relation to an increasing progress parameter representing the progress of the amplification process; determining a characteristic value of the progress parameter for the target nucleic acid on the basis of measurement results related to the amount of amplification product for the target nucleic acid; at least for certain cases: determining a characteristic value of the progress parameter also for the control nucleic acid on the basis of measurement results related to the amount of amplification product for the control nucleic acid; quantifying the original amount of target nucleic acid in the test sample according to predefined or selected quantification scheme on the basis of at least the characteristic value determined for the target nucleic acid.

In particular implementations, the method further comprises the step of selecting between a plurality of quantification schemes of different types, wherein at least one quantification scheme provides for qualification of the original amount of target nucleic acid in the test sample without reference to any characteristic value for the control nucleic acid and at least one quantification scheme provides for quantification of the original amount of target nucleic acid in the test sample with reference to the characteristic value for the control nucleic acid.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2 shows an exemplary PCR amplification growth curve before (FIG. 2a) and after (FIG. 2b) normalization of the fluorescence measurement results.

FIG. 9 shows two possibilities for a calibration on the basis of a standard for high target concentrations.

FIGS. 10a and 10b show an example for a standard quantification on the basis of amplification results referring to the target and an internal control.

FIGS. 11a and 11b show two possibilities for an exceptional quantification on the basis of amplification results referring to the target only.

FIG. 12 shows the print on the packet of a HBV test kit used to evaluate the invention and to provide illustrative experimental results shown herein.

FIG. 13 shows growth curves for a dilution series of HBV plasmid target and internal controls obtained on basis of the HBV test according to FIG. 12.

FIG. 15 shows growth curves for a second dilution series (second research lot) of HBV plasmid target and internal controls obtained on basis of the HBV test according to FIG. 12.

FIGS. 17a and 17b give examples for calibration formulas, which can alternatively be used for the quantification of the initial target titer.

Like reference symbols in the various drawings indicate like elements.

DETAILED DESCRIPTION

Figure 1A:
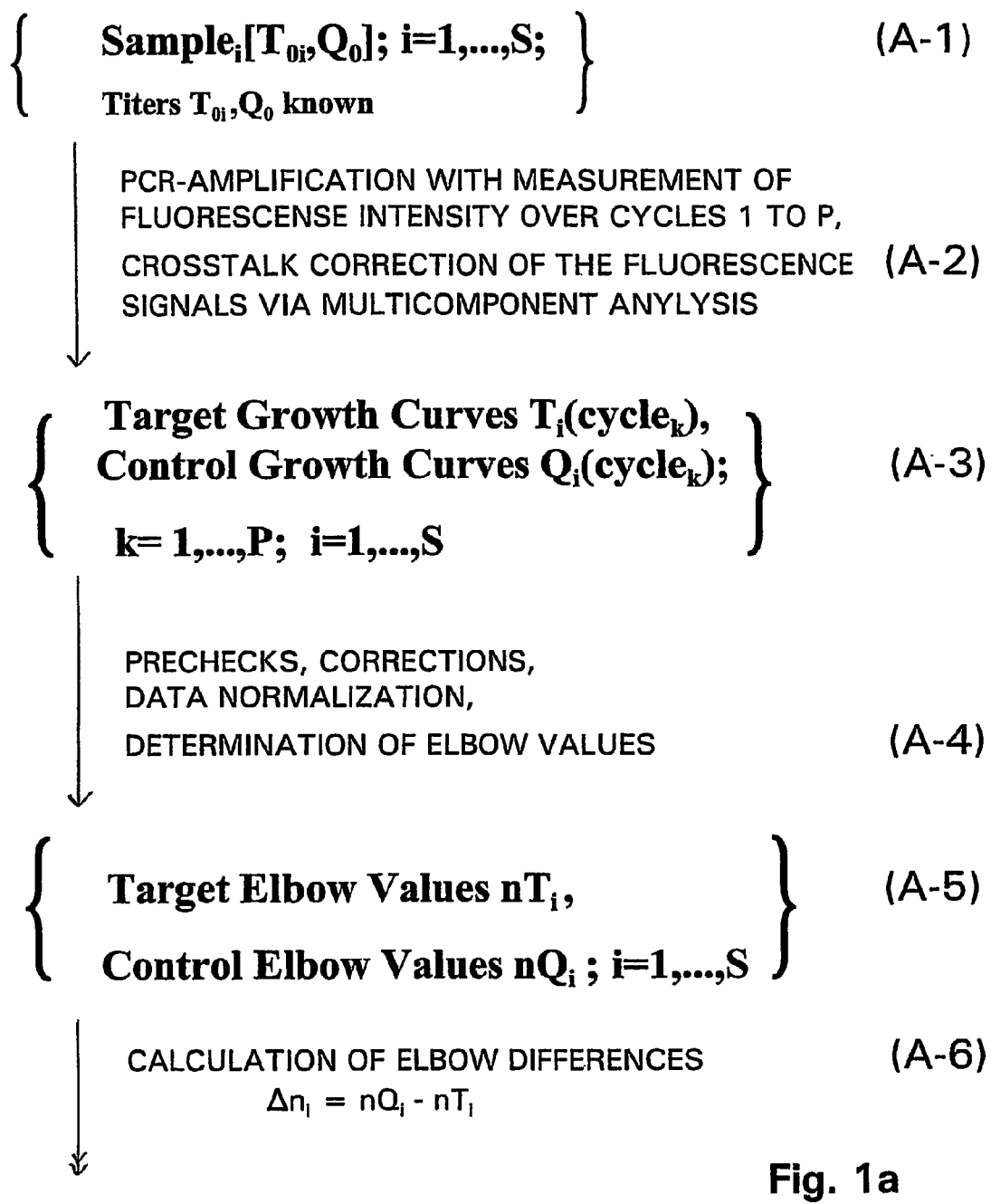
FIGS. 1A and B show a method for calibrating the quantification of nucleic acids on the basis of PCR amplification using a calibration formula based on a standard.

In order to obtain reliable and reproducible quantitative data, many different PCR based protocols have been developed. Generally, two different basic principles can be discriminated conventionally, namely i) competitive PCR (or RT-PCR) using internal standards and ii) quantification of target DNA by initial generation of a calibration curve. It is referred in this respect to Siebert, Molecular Diagnosis of Infectious Diseases (ed. Udo Reischl, Humana Press, Totowa, N.J., p. 55-79, 1998).

The competitive PCR or RT-PCR allows an end point determination of the amount of PCR product formed in the plateau phase of the amplification reaction. For example, a specific target sequence is coamplified together with a dilution series of an internal standard of a known copy number. The initial copy number of the target sequence is extrapolated from the mixture containing an identical PCR product quantity of standard and target sequence (Zimmermann and Mannhalter, BioTechniques 21:280-279, 1996). A disadvantage of this method is that the measurement occurs in the saturation region of the amplification reaction.

A major improvement in the generation of quantitative data derives from the possibility of measuring the kinetics of a PCR reaction by on-line detection. This has become possible by means of detecting the amplicon through fluorescence monitoring. Examples of such techniques are disclosed in detail in WO 97/46707, WO 97/46712 and WO 97/46714 (Wittwer et al.).

Higuchi et al. (BioTechnology 11, 1026-2030, 1993) disclosed an approach for initial template quantification using fluorescence monitoring at each cycle. A fluorescence threshold level was used to define a fractional cycle number related to initial template concentration. Specifically, the log of the initial template concentration was found to be inversely proportional to the fractional cycle number (CT), defined as the intersection of the fluorescence versus cycle number curve with the fluorescence threshold.

Kinetic real-time quantification in the exponential phase of PCR can be effected on basis of an internal standard as well as of an external standard. Generally, the formation of PCR products is monitored in each cycle of the PCR. The amplification is usually measured in thermocyclers that have additional devices for measuring fluorescence signals during the amplification reaction. A typical example of this is the Roche Diagnostics Light Cycler (Cat. No. 2 0110468).

The amplification products are for example detected by means of fluorescent-labeled hybridization probes that only emit fluorescence signals when they are bound to the target nucleic acid or in certain cases also by means of fluorescent dyes that bind to double-stranded DNA. A defined signal threshold is determined for all reactions to be analyzed and the number of cycles, cp, required to reach this threshold value is determined for the target nucleic acid and—if an internal standard or internal control (possibly housekeeping gene) is used—for the reference nucleic acid. The absolute or relative copy numbers of the target molecule can be determined on basis of the cp values obtained for the target nucleic acid and the reference nucleic acid or—where an external standard is used—on basis of the respective cp value obtained for the target molecule and a standard curve constructed on basis of separate amplification results for the reference nucleic acid (e.g. dilution series of the reference nucleic acid) (Gibson et al., Genome Research 6:995-1001, 1996; Bièche et al., Cancer Research 59:2759-2765, 1999; WO 97/46707; WO 97/46712; WO 97/46714).

The use of external standards has the advantage that the standard and target nucleic acid are amplified in separate reaction vessels. In this case a standard can be used which has an identical sequence to the target nucleic acid. However, systematic errors can occur in this type of quantification, for example due to inhibitory components that impair the efficiency of the subsequent PCR reaction. These errors can be excluded by using internal standards, i.e. by amplifying the standard and target nucleic acid in one reaction vessel. However, a disadvantage of this method is that standards have to be used that have different sequences compared to the target nucleic acid to be analyzed in order to be able to distinguish between the amplification of the standard and target nucleic acid. This can lead to systematic errors in the quantification as well, since different efficiencies of the PCR application cannot be excluded when the sequences are different.

With respect to the issue use of internal or external controls or standards we distinguish the following approaches:

a) External controls (the term external standards is also appropriate) are amplified by subjecting different amounts of a known DNA to PCR to obtain a standard curve. The amount of sample DNA amplified separately, possibly in parallel, can be derived directly by interpolation of the standard curve. Preconditions for this quantification method are that the efficiency of both PCRs, that of the standard DNA and that of the sample DNA, are sufficiently identical and that the amplification reactions are in the exponential phase.

b) PCRs using internal controls (IC) or internal standards (IQS, Internal Quantification Standards) can be performed as multiplex or competitive PCR. In multiplex PCR the primer pair for the IC is derived from a different DNA molecule than the primer pair for sample DNA whereas in competitive PCR the same primer pair is used for both, the IC and sample DNA. Preconditions for quantification by multiplex PCR are the same as for PCRs using external controls. Multiplex PCR as compared to PCRs using external standards has, however, the advantage, that both IC DNA and sample DNA are amplified in the same tube and thus problems due to variations in tube consistency or position in the thermal cycler are eliminated. In competitive PCR, amplicons generated from the IC and sample DNA by the same primer pair have to be differentiated. During the amplification both IC DNA and sample DNA compete for the same primer pair. If the amount of initial template DNAs (IC and sample DNA) is unequal, PCR product yield is shifted to the credit of the DNA being in excess. Only when the amount of initial template DNA is equimolar, product yield for IC and sample DNA is identical, as far as identical amplification efficiency applies.

As already indicated, the possibility of measuring the kinetics of an amplification reaction has become enormously facilitated since there are instruments and methods available, wherein the generation of the amplification product can be measured continuously by spectroscopic detection principles, in particular by means of fluorescence. An example for a suitable instrument is described in detail in Wittwer et al., BioTechniques 22, No. 1, 176-181 (1997).

Several detection formats that are based on target dependent fluorescent signaling, and which enable continuous monitoring of the generation of amplification products, have been disclosed (reviewed in Wittwer et al., BioTechniques, 22, No. 1, 130-138, 1997). These detection formats include but are not limited to:

1. Use of Fluorescent Double-stranded DNA Recognizing Compounds

Since the amount of double-stranded amplification product usually exceeds the amount of nucleic acid originally present in the sample to be analyzed, double-stranded DNA specific dyes can be used, which upon excitation with an appropriate wavelength show enhanced fluorescence only if they are bound to double-stranded DNA. Dyes that do not affect the efficiency of the PCR reaction, for example, SYBR Green I, are used advantageously.

2. Increased Fluorescence Resonance Energy Transfer upon Hybridization

For this detection format, two oligonucleotide hybridization probes each labelled with a fluorescent moiety are used which are capable of hybridizing to adjacent but not overlapping regions of one strand of the amplification product. When hybridized to the target DNA, the two fluorescent labels are brought into close contact, such that fluorescence resonance energy transfer (FRET) between the two fluorescent moieties can take place. As a consequence, the hybridization can be monitored through excitation of the donor moiety and subsequent measurement of fluorescence emission of the second acceptor moiety.

In a similar embodiment, only one fluorescently labelled probe is used, which together with one appropriately labelled primer may also serve as a specific FRET pair (Bernard et al., Analytical Biochemistry 255, p. 101-107, 1998).

3. Detection Principle as Used in the TaqMan™ Instrument

In order to detect the amplification product, a single-stranded hybridization probe is used, which is labelled with a fluorescent entity, the fluorescence emission of which is quenched by a second label on the same probe which may act as a quenching compound on basis of Förster-type energy transfer effects. During the annealing step of the PCR reaction, the probe hybridizes to its target sequence, and, subsequently, during the extension of the primer, the DNA polymerase having a 5'-3'-exonuclease activity digests the hybridization probe into smaller pieces, such that the fluorescent entity is separated from the quencher compound. After appropriate excitation, fluorescence emission can be monitored as an indicator of accumulating amplification product.

4. Molecular Beacons

Similar to the probes/formats used in the TaqMan™ instrument, a molecular beacon oligonucleotide is labelled with a fluorescent compound and a quencher compound, which due to the secondary structure of the molecule are in close vicinity to each other. Upon binding to the target DNA, the intramolecular hydrogen bonding is broken, and the fluorescent compound located at one end of the probe is separated from the quencher compound, which is located at the opposite end of the probe (Lizardi et al., U.S. Pat. No. 5,118,801).

A method for determining an unknown starting quantity of a target nucleic acid sequence in a test sample is known from US 2002/0031768 A1 (McMillan et al.). The unknown starting quantity of the target nucleic acid sequence in the test sample and known starting quantities of a calibration nucleic acid sequence in respective calibration samples are amplified. For each of the nucleic acid sequences a respective threshold value is determined, using a derivative of a growth curve derived for the sequence. Using the threshold value determined for the target sequence and a calibration curve derived from the threshold values determined for the calibration nucleic acid sequence the starting quantity of the target nucleic acid is determined. McMillan et al. discloses also instrumentation and apparatus that can be used for the implementation of the method. Further, methods for determining a starting quantity of a nucleic acid sequence in a sample using quantitative internal controls or using internal standards are disclosed, as for example in US 2002/0034745 A1, US 2002/0034746 A1 and US 2002/0058282 A1.

The quantification of analytes on basis of a derivative calculated from a growth curve is also known from EP 1 041 158 A2 (compare also U.S. Pat. Nos. 6,303,305 B1, 6,503,720 B2 and US 2002/0028452 A1, Wittwer et al.).

EP 1 138 783 A2 and EP 1 138 784 A2 (compare also US 2002/0058262 A1, Sagner et al.) disclose methods for absolute and relative quantification of a target nucleic acid involving the determination of an amplification efficiency. It is referred to internal standards as well as to external standards.

U.S. Pat. No. 5,389,512 (Sninsky et al.) discloses a method for determining the relative amount of a nucleic acid sequence in a sample by the polymerase chain reaction. The method involves the simultaneous amplification of the nucleic acid segment and a second nucleic acid segment present in a sample. The amount of amplified DNA from each segment is determined and compared to standard curves to determine the amount of the nucleic acid segment present in the sample before the amplification expressed as a ratio of the first segment to second segment. Two standard curves are used, one referring to the amplification of the first segment and the other referring to the amplification of the second segment.

U.S. Pat. No. 5,476,774 (Wang et al.) provides a further method for determining the amount of a target acid segment in a sample by polymerase chain reaction. The method involves the simultaneous amplification of the target nucleic acid segment and an internal standard nucleic acid segment. The amount of amplified DNA from each segment is determined and compared to standard curves to determine the amount of the target nucleic acid segment present in the sample prior to amplification.

Instrumentation and apparatus which can be used advantageously in the context of PCR-quantification are disclosed in various publications, e.g. EP 0 953 379 A1, disclosing an apparatus for simultaneously monitoring reactions taking place in a plurality of reaction vessels, EP 0 953 837 A1, disclosing a fluorescence light measuring device which can be used in such an apparatus, and EP 0 955 097 A1, disclosing a thermal cycler for performing amplification of nucleic acids.

The above-mentioned documents are completely incorporated by reference in the disclosure of the present application. Further, it is referred in this respect to Ullmann's Encyclopedia of Industrial Chemistry, 6. ed., Vol. 28, section "Polymerase Chain Reaction" (pages 125 to 159), in particular chapter 10 "Quantitative PCR" (pages 140 to 144, WILEY-VCH-Verlag, Weinheim, Germany 2003), which is also incorporated by reference in its entirety.

The invention refers to, and, according to a first, more general, aspect, provides a method for quantification of at least one target nucleic acid in a test sample or in a plurality of test samples which comprises the steps of:

providing at least one target nucleic acid together with at least one internal control in a common test sample, said internal control comprising a defined initial amount of a control nucleic acid different from said target nucleic acid;

amplifying said target nucleic acid and said control nucleic acid within said test sample in a common nucleic acid amplification process;

measuring the amount of amplification product or a quantity indicating the amount of amplification product for said target nucleic acid and said control nucleic acid during said amplification in relation to an increasing progress parameter representing the progress of said amplification process;

determining a characteristic value of said progress parameter for said target nucleic acid on basis of measurement results related to the amount of amplification product for said target nucleic acid;

determining a characteristic value of said progress parameter also for said control nucleic acid on basis of measurement results related to the amount of amplification product for said control nucleic acid;

quantifying the original amount of target nucleic acid in said test sample according to a predetermined quantification scheme, said quantification scheme providing for the quantification of the original amount of target nucleic acid in said test sample on basis of the characteristic value for said target nucleic acid, the characteristic value for said control nucleic acid and associated reference data.

Measuring the amount of amplification product or a quantity indicating the amount of amplification product can be done directly, for example, by determining a characteristic of the amplification product, or indirectly, for example, by measuring a quantity that is associated to or correlated with the amount of amplification product.

This method for quantification allows the use of an external standard in combination with an internal control or standard, so that on the one hand the standard nucleic acid can have the same sequence as the target nucleic acid and on the other hand changes between the efficiencies of the respective PCR reaction in different reaction vessels can be taken into account to a certain extent on basis of the internal control or standard. Advantageous embodiments of the above defined method result implicitly from the following explanations.

It was observed that the amplification of different nucleic acids within a common sample in a common nucleic acid amplification process can lead to effects and problems which are caused by the competition between the individual amplification reactions with respect to the different nucleic acids. With respect to PCR and RT-PCR there will be competition for nudeotides, enzymes and other ingredients contained in the PCR reaction mix and, in the competitive PCR, when the respective nucleic acids have identical primer binding sides, for the primers. In particular, competitive amplification of an internal quantification standard or internal control and the target within a method for quantification can lead to decreased sensitivity of the method or even to failure of the quantification of the original amount of target according to a quantification scheme used when there is a strong imbalance between the amounts of target and internal control at the beginning of the amplification reaction, in particular PCR reaction. Either the internal control of the target will be detected with decreased sensitivity or will not be detected in an extent that allows quantification. For example, there can be a dropout of target growth curves, if the concentration of the internal control concentration is too high, or there can be a dropout of internal control growth curves, if the target concentration is too high. Accordingly, the dynamic range of the method and a corresponding system is limited. Targeted specifications for the linear range can only be met either for a lower range or an upper range on basis of certain reagent lots. Of course, it is possible to provide different reagent lots aiming to the lower range and to the upper range. This solution, however, is cumbersome from a practical point of view, and there remains a considerable risk to fail at least at one end (the lower or the upper) due to the labile situation at the quantification/detection limits.

According to a first, more general, aspect, it is an object of the invention to provide a method for quantification of at least one target nucleic acid in a test sample or a plurality of test samples which is less prone to systematic errors than methods of the prior art. This object is achieved by the method defined in the foregoing.

According to a second, more specific, aspect, it is an object of the invention to provide a method for quantification of at least one target nucleic acid in a test sample or in a plurality of test samples that has an extended dynamic range.

To solve both objects, in one implementation, a method for quantification of at least one target nucleic acid in a test sample or in a plurality of test samples comprises the steps of:

a) providing at least one target nucleic acid together with at least one internal control in a common test sample, said internal control comprising a defined initial amount of a control nucleic acid different from said target nucleic acid;

b) amplifying said target nucleic acid and said control nucleic acid within said test sample in a common nucleic acid amplification process;

c) directly or indirectly measuring the amount of amplification product or a quantity indicating the amount of amplification product for said target nucleic acid and said control nucleic acid during said amplification in relation to an increasing progress parameter representing the progress of said amplification process;

d) determining a characteristic value of said progress parameter for said target nucleic acid on basis of measurement results related to the amount of amplification product for said target nucleic acid;

e) if certain predefined conditions referring to the measured amount of amplification product for said control nucleic acid apply, determining a characteristic value of said progress parameter also for said control nucleic acid on basis of measurement results related to the amount of amplification product for said control nucleic acid;

f) selecting between a plurality of quantification schemes according to at least one predefined selection criterion, said selection being effected directly or indirectly on basis of at least one of said measurement results related to the amount of amplification product for said target nucleic acid, measurement results related to the amount of amplification product for said control nucleic acid and said characteristic value or values, wherein at least one quantification scheme of a first type provides for a quantification of the original amount of target nucleic acid in said test sample on basis of the characteristic value for said target nucleic acid, the characteristic value for said control nucleic acid and associated reference data, wherein at least one quantification scheme of a second type provides for a quantification of the original amount of target nucleic acid in said test sample on basis of the characteristic value for said target nucleic acid and associated reference data without reference to any characteristic value for said control nucleic acid, g) quantifying the original amount of target nucleic acid in said test sample according to the selected quantification scheme on basis of at least the characteristic value determined for said target nucleic acid.

In this implementation, the dynamic range can be extended by using different quantification schemes for different ranges, for example a quantification scheme of the first type for a lower and medium range and, if necessary or appropriate, a quantification scheme of the second type for an upper range. In particular, a dropout of the internal control growth curve in situations where the target concentration is too high does not affect a quantification scheme of the second type.

Dependent on the details of the quantification scheme of the second type and the associated reference data used, it is in principle possible to obtain a quantification of a quality that corresponds more or less to the quality of quantification conventionally obtained on basis of a quantification using an external standard and no internal control. If the quantification scheme or quantification schemes of the second type refer to an upper range of the targeted linear range of the quantification method, then the situation on a whole is even better, since—in the context of PCR amplification—high target concentrations mean fewer PCR cycles to achieve a certain target yield, so that changes in the amplification factor per PCR cycle are less relevant. To say it differently: Since the accuracy of a titer measurement scales inversely with the number of PCR cycles, the error of high target yields obtained on basis of high initial target concentrations is relatively small, because fewer cycles are involved in the quantification process. Of course, the advantages of the use of an internal control such as an additional validation by considering the internal control amplification results will not be obtained on basis of the quantification scheme of the second type. This, however, is in any case better than obtaining no quantification or a completely wrong quantification.

In another implementation, a quantification scheme of the second type is selected when at least one of the following conditions apply:

i) no characteristic value for said control nucleic acid was determined, ii) the characteristic value for said control nucleic acid exceeds a predefined threshold value, iii) the characteristic value for said target nucleic acid falls short of a predefined threshold value, iv) the characteristic value for said control nucleic acid exceeds the characteristic value for said target nucleic acid by at least a predefined amount, v) the amount of amplification product or the quantity indicating the amount of amplification product for said control nucleic acid as measured or estimated for a final stage or near final stage of the amplification process falls short of a predefined minimum plateau value, vi) the amount of amplification product or the quantity indicating the amount of amplification product for said control nucleic acid as measured or estimated for a momentary state of the amplification process associated to the characteristic value for the target nucleic acid falls short of a predefined threshold value, the amount of amplification product, or the quantity indicating the amount of amplification product for said target nucleic acid as measured or estimated for said momentary state of the amplification process.

According to one approach, a quantification scheme of the first type is selected when a characteristic value for said control nucleic acid was determined. Alternatively, a quantification scheme of the first type can be selected when a characteristic value for said control nucleic acid was determined and at least one of the following conditions apply:

ii) the characteristic value for said control nucleic acid falls short of a predefined threshold value, iii) the characteristic value for said target nucleic acid exceeds a predefined threshold value, iv) the characteristic value for said control nucleic acid falls short of a threshold value defined in relation and greater than the characteristic value for said target nucleic acid, v) the amount of amplification product or the quantity indicating the amount of amplification product for said control nucleic acid as measured or estimated for a final stage or near final stage of the amplification process exceeds of a predefined minimum plateau value, vi) the amount of amplification product or the quantity indicating the amount of amplification product for said control nucleic acid as measured or estimated for a momentary state of the amplification process associated to the characteristic value for the target nucleic acid exceeds a predefined threshold value, the amount of amplification product, or the quantity indicating the amount of amplification product for said target nucleic acid as measured or estimated for said momentary state of the amplification process.

The reference data associated to said or respective quantification scheme of the first type can be calibration data determined or provided by A) providing at least one standard together with at least one internal control in a common sample, said standard comprising a defined initial amount of a standard nucleic acid, said internal control comprising a defined initial amount of a control nucleic acid, said standard nucleic acid and said control nucleic acid being different;

B) amplifying said standard and said internal control within said sample in a common nucleic acid amplification process;

C) directly or indirectly measuring the amount of amplification product or a quantity indicating the amount of amplification product for said standard nucleic acid and said control nucleic acid during said amplification in relation to an increasing progress parameter representing the progress of said amplification process;

D) determining a characteristic value of said progress parameter for said standard nucleic acid on basis of measurement results related to the amount of amplification product for said standard nucleic acid;

E) determining a characteristic value of said progress parameter for said control nucleic acid on basis of measurement results related to the amount of amplification product for said control nucleic add;

H) relating said initial amount of standard nucleic acid on the one hand and said characteristic values on the other hand with reference to said quantification scheme of the first type to provide said calibration data associated to said quantification scheme of the first type.

With respect to the reference data associated to said or respective quantification scheme of the second type two approaches are contemplated. According to a first approach the reference data are calibration data determined or provided on basis of AA) providing at least one standard in a sample, said standard comprising a defined initial amount of a standard nucleic acid;

BB) amplifying said standard in a nucleic acid amplification process;

CC) directly or indirectly measuring the amount of amplification product or a quantity indicating the amount of amplification product for said standard nucleic acid during said amplification in relation to an increasing progress parameter representing the progress of said amplification process;

DD) determining a characteristic value of said progress parameter for said standard nucleic acid on basis of measurement results related to the amount of amplification product for said standard nucleic acid;

HH) relating said initial amount of standard nucleic acid on the one hand and said characteristic value on the other hand with reference to said quantification scheme of the second type to provide said calibration data associated to said quantification scheme of the second type.

According to a second approach, said reference data associated to said or respective quantification scheme of the second type are calibration data determined or provided on basis of steps A) to D) and on basis of HH) relating said initial amount of standard nucleic acid on the one hand and said characteristic value associated to said standard nucleic acid on the other hand with reference to said quantification scheme of the second type to provide said calibration data associated to said defined initial amount of said control nucleic acid being amplified together with said standard nucleic acid can correspond to said defined initial amount of said control nucleic add being amplified together with said target nucleic add. Said control nucleic add, which is amplified together with said standard nucleic acid, can correspond to said control nucleic add which is amplified together with said target nucleic acid. Said standard can be an external standard, said sample being different from said test sample. Said standard nucleic acid can correspond to said target nucleic acid.

At least one and possibly all of said steps A) to H) and possibly HH) or/and at least one or possibly all of said steps AA) to HH) can be effected simultaneously to respective steps a) to g).

Steps A) to E) or/and steps AA) to DD) can be effected before or after effecting steps a) to e). Steps A) to H) and possibly HH) or/and steps AA) to HH) can be effected before effecting steps a) to g). For example, said steps can be effected by the manufacturer of a quantification kit. In particular, said calibration data associated to said quantification scheme of the first type or/and said calibration data associated to said quantification scheme of the second type can be provided together with constituents of a quantification kit.

In step A) a dilution series of said standard nucleic acid can be provided, each dilution within a respective sample together with said internal control, that steps B) to E) are effected with respect to all samples of said dilution series, and that step H) comprises:

relating the initial amounts of standard nucleic acid of said samples on the one hand and the characteristic values determined for said samples on the other hand with reference to said quantification scheme of the first type to provide said calibration data associated to said quantification scheme of the first type.

Further, step HH), can comprise:

relating the initial amount of standard nucleic acid of a selected or predefined one of said samples on the one hand and the characteristic value associated to said standard nucleic acid determined for said sample being selected on the other hand with reference to said quantification scheme of the second type to provide said calibration data associated to said quantification scheme of the second type.

Alternatively step HH) can comprise:

relating the initial amounts of standard nucleic acid of said samples on the one hand and the characteristic values associated to said standard nucleic acid determined for said samples on the other hand with reference to said quantification scheme of the second type to provide said calibration data associated to said quantification scheme of the second type.

In step AA) only one sample including a selected defined initial amount of said standard nucleic acid is provided. However, it can be advantageous, if in step AA) a dilution series of said standard nucleic acid is provided, each dilution within a respective sample, wherein steps BB) to DD) are effected with respect to all samples of said dilution series, and wherein step HH) comprises:

relating the initial amounts of standard nucleic of said samples on the one hand and the characteristic values determined for said samples on the other hand with reference to said quantification scheme of the second type to provide said calibration data associated to said quantification scheme of the second type.

Irrespective of how the calibration data associated to said quantification scheme of the second type are provided, said calibration data can include a fixed amplification efficiency. Alternatively, in step g) the calibration data associated to said quantification scheme of the second type can be used together with a fixed amplification efficiency for the quantification of the original amount of target nucleic in said test sample according to the quantification scheme of the second type.

Generally, a theoretical amplification efficiency of said amplification process can be used as said fixed amplification efficiency. Said fixed amplification efficiency can be determined on basis of steps A) to H) or on basis of steps AA) to HH), said fixed amplification efficiency being included in or derived from said calibration data associated to said quantification scheme of the first type or being included in said calibration data associated to said quantification scheme of the second type.

The determination of the fixed amplification efficiency on basis of amplification results can lead to more precise quantification on basis of the quantification scheme of the second type.

Generally, said amplification process (or the respective amplification process) can be effected in cycles. This is in particular true for conventional PCR and RT-PCR processes already referred to. If said (the respective) amplification process is effected in cycles, a cycle number indicating the number of elapsed cycles can be used as progress parameter. However, irrespectively whether said amplification process is effected in cycles or not, it is possible to use an elapsed time of amplification as progress parameter. With reference to step c) and also the corresponding step of the solution according to the first, more general, aspect this step can comprise:

measuring, at a plurality of different times during amplification, at least one signal whose intensity is related to the quantity of the respective nucleic acid being amplified.

This is also suggested with respect to step C) and with respect to step CC). The signal being measured can be an optical signal, for example fluorescence radiation emitted from fluorescent entities, in particular dyes, associated to the respective nucleic acid, fluorescent label hybridization probes associated to the respective nucleic acid or the like.

Further, at least one of step d) and step e) and of the corresponding steps of the solution according to the first, more general, aspect can comprise or be based on:

deriving a growth curve from the respective measurement results, possibly the measurements of the respective signal.

This is also suggested with respect to at least one of step D) and E) and with respect to step DD).

Further, at least one of step d) and step e) and at least one of the corresponding steps of the solution according to the first, more general, aspect can comprise:

identifying a characteristic of the respective growth curve or of a derivative calculated of the respective growth curve, determining the characteristic value associated with the respective characteristic.

This is also suggested with respect to at least one of step D) and step E) and with respect to step DD).

The characteristic of the respective growth curve can correspond to a crossing of a threshold by the growth curve, said threshold being predefined to represent an unnormalized growth value or being determined on basis of respective measurement results to represent a normalized growth value. If such a characteristic of the growth curve (for example, a normalized growth curve) is used, then it is generally not necessary to calculate a derivative of the growth curve.

With respect to the possibility to use a derivative calculated of the respective growth curve, it is suggested that the characteristic of the respective derivative corresponds to a positive peak or a negative peak or a zero crossing of the derivative. The derivative can be the first or second derivative of the respective growth curve.

The determination of the respective characteristic value can involve the interpolation of the growth curve between growth curve points representing a respective measurement, or the interpolation of a calculated derivative curve between respective points, to give a characteristic value not necessarily corresponding to a value of the progress parameter for which a measurement was effected. In particular, a fractional cycle number can be determined as characteristic value.

Generally, said characteristic value or values represent a direct or indirect measure of at least one of the amplification and the original amount or defined initial amount of the respective nucleic acid.

In one implementation, according to said or at least one quantification scheme of the first type, a secondary characteristic value is determined from said characteristic value for said target nucleic acid or standard nucleic acid, respectively, and said characteristic value of said control nucleic acid. The secondary characteristic value represents a direct or indirect measure of at least one of the amplification and the original amount of said target nucleic acid or initial amount of said standard nucleic acid, respectively, relative to at least one of the amplification and the defined initial amount of said control nucleic acid. In this case the original amount of target nucleic acid can be quantified on basis of said secondary characteristic value and said reference data associated thereto.

It is further suggested that step H) comprises:

relating said initial amount of standard nucleic acid on the one hand and said secondary characteristic value on the other hand with reference to said quantification scheme of the first type to provide said calibration data associated to said quantification scheme of the first type.

According to said or at least one quantification scheme of the first type, a ratio value representing the ratio of the characteristic value for said target nucleic acid or standard nucleic acid, respectively, and the characteristic value of said control nucleic acid can be determined. In this case the original amount of target nucleic acid can be quantified on basis of said ratio value and said reference data associated thereto.

In this context, step H) can comprise:

relating said initial amount of standard nucleic acid on the one hand and said ratio value on the other hand with reference to said quantification scheme of the first type to provide said calibration data associated to said quantification scheme of the first type.

According to said or at least one quantification scheme of the first type, a difference value representing the difference between the characteristic value for said target nucleic acid or standard nucleic acid, respectively, and the characteristic value of said control nucleic acid can be determined. In this case, the original amount of target nucleic acid can be quantified on basis of said difference value and said reference data associated thereto.

In this context it is further suggested said step H) comprises:

relating said initial amount of standard nucleic acid on the one hand and said difference value on the other hand with reference to said quantification scheme of the first type to provide said calibration data associated to said quantification scheme of the first type.

A plurality of secondary characteristic values (e.g. ratio values or difference values) can be used, which correspond to the secondary characteristic values of the samples of the dilution series. In this case step H) may comprise:

relating said initial amounts of standard nucleic acid of said samples on the one hand and said secondary characteristic values determined for said samples on the other hand with reference to said quantification scheme of the first type to provide said calibration data associated to said quantification scheme of the first type.

To provide said calibration data generally a calibration equation or calibration formula can be used which represents a relation between the initial amount of said standard nucleic acid, the initial amount of said internal control and said characteristic values (i.e. the characteristic value of said progress parameter for said standard nucleic acid and the characteristic value of said progress parameter for said control nucleic acid) or the secondary characteristic value.

With reference to PCR amplification the relation between initial numbers of nucleic acid molecules and the amplified product is described by an exponential function:

$$y = y_0 (1+\epsilon)^n$$

with y=product yield (amount of DNA after amplification)
$y_0$=amount of template DNA prior to PCR
$\epsilon$=efficiency of the amplification process
n=number of cycles Denoting the product yield for the target or standard nucleic acid as T, the initial amount of target or standard nucleic acid prior to PCR as $T_0$, the efficiency of the PCR amplification for the target or standard nucleic acid as $\epsilon_T$, the cycle number of the PCR process determined as characteristic value for the amplification of the target or standard as $n_T$, the product yield of the internal standard or internal control nucleic acid as Q, the initial amount of internal standard or internal control nucleic acid prior to PCR as $Q_0$, the efficiency of the PCR amplification with respect to the amplification of the internal standard or internal control as $\epsilon_Q$, and the cycle number of the PCR process determined as characteristic value for the amplification of the internal standard or internal control as $n_Q$, the difference $\Delta n = n_Q - n_T$ can be used as secondary characteristic value. On basis of the assumption that the respective yield T and Q associated to the respective cycle number $n_T$ and $n_Q$ are equal or proportional to each other, the following equation can be derived:

$$\log(T_0/Q_0) = \log f + \Delta n \log(1+\epsilon)$$

wherein $\epsilon=\epsilon_T=\epsilon_Q$ has additionally been assumed. This equation can be used as calibration equation. However, it has been observed that an equation of the form $$\log(T_0/Q_0)=a\,\Delta n^2+b\,\Delta n+c$$

may be more appropriate to describe data obtained in practice. Accordingly this equation or the equation $$T_0=Q_0\,10^P$$

with $$P=a\,\Delta n^2+b\,\Delta n+c$$

can be used advantageously as quantification equation. It may be appropriate to additionally take into account a so-called volume factor v and a so-called recovery factor r, so that $$T_0=(v/r)Q_0\,10^P$$

is obtained.

With reference to one of these calibration equations, the determination of the calibration data involves basically the determination of the respective equation, in particular of the second order polynomial constant a, the first order polynomial constant b, the zero order polynomial constant c and possibly the volume factor v and the recovery r (default value for example 1.00). On basis of the measurement results and in particular on basis of the determined characteristic values, e.g. the determined secondary characteristic values $\Delta n$, the polynomial constants can be determined by fitting the respective equation to the respective data actually obtained on basis of effecting steps A) to E). This fitting can for example be done by the RMS fitting method. On basis of the respective parameters a, b, c and possibly v and r, in step g) and correspondingly in the respective step of the inventive solution according to the first, more general, aspect, the original amount of target nucleic acid in the test sample can be determined using the selected quantification scheme of the first type, with the characteristic value for the control nucleic acid and the characteristic value for the target nucleic acid or the secondary characteristic value obtained therefrom (in the example considered here the values $n_T$ and $n_Q$ or the value $\Delta n$) being used as input values.

It should be remarked that as characteristic values for the respective nucleic acids so-called elbow values can be used. As shown in FIG. 2, the elbow value is the (fractional) cycle number in which the growth curve is approximately equal to a predetermined threshold value and in which exponential growth is still true.

The foregoing makes it sufficiently clear that the amplification process can comprise a polymerase chain reaction (PCR) process. Further, it has already been indicated that the amplification process can comprise or be part of a reverse transcriptase polymerase chain reaction (RT-PCR) process.

Said target nucleic acid or standard nucleic acid and said control nucleic acid can be competitively amplified in said amplification process on basis of the same primers for the target nucleic acid or standard nucleic acid and for said control nucleic acid.

In principle, there are many possible ways that the amplified nucleic acids can be detected. The amplified nucleic acids can be detected by means of a detection format that is based on nucleic acid dependent fluorescent signaling. In particular, it can be advantageous if the amplified nucleic acids are detected by means of a detection format that allows continuous monitoring of the generation of amplification products. For example, the amplified nucleic acids can be detected on basis of at least one fluorescent-labelled hybridization probe or/and at least one fluorescent-labelled primer. In one embodiment, a fluorescent-labelled hybridization probe is used which is labelled with a fluorescent entity and with a quenching entity, a separation of the fluorescent entity and the quenching entity from each other occurring on hybridization of the hybridization probe to its target sequence, the separated fluorescent entity being optically excitable to emit fluorescence.

Another possibility is the use of a first fluorescent-labelled hybridization probe and a second fluorescent-labelled hybridization probe, the first hybridization probe being labelled with a fluorescent acceptor entity and the second hybridization probe being labelled with a fluorescent donor entity, wherein the first and the second hybridization probe are adapted to hybridize to neighboring target sequences, and wherein on hybridization to neighboring target sequences the fluorescent acceptor entity is excitable to emit fluorescence via optical excitation of the fluorescent donor entity and fluorescence resonance energy transfer from the fluorescent donor entity to the fluorescent acceptor entity.

Further, one might use a fluorescent-labelled hybridization probe and a fluorescent-labelled primer, one thereof being labelled with a fluorescent acceptor entity and the other thereof being labelled with a fluorescent donor entity, wherein the hybridization probe is adapted to hybridize to a target sequence neighboring to the primer, and wherein on hybridization of the hybridization probe to its target sequence the fluorescent acceptor entity is excitable to emit fluorescence via optical excitation of the fluorescent donor entity and fluorescence resonance energy transfer from the fluorescent donor entity to the fluorescent acceptor entity.

In particular, amplified nucleic acids can be detected on basis of FRET hybridization probes, so-called molecular beacons or probes as used in the TaqMan™ instrument.

It is also possible to detect amplified nucleic adds on basis of a DNA-binding dye, which is optically excitable to emit fluorescence and which shows enhanced fluorescence when bound to a double standard DNA.

The method according to the invention can advantageously be performed using a COBAS TaqMan™ system as provided by Roche Diagnostics.

From the embodiment discussed in the foregoing it is made clear that the method of the invention can be a method for absolute quantification of the respective target nucleic acid. However, it is not ruled out that the method is a method for relative quantification of the respective target nucleic acid.

In another implementation, the method of the invention can additionally comprise the steps of:
  selecting between a quantification of said target nucleic acid in said test sample and between a determination of presence or non-presence of said target nucleic acid in said test sample,
  if selected: determining the presence or non-presence of said target nucleic acid in said test sample on basis measurement results obtained in step c), possibly leaving out steps d) to g).

The invention further provides a quantification kit containing agents and reference or calibration data to carry out the method of the invention.

Figure 24:
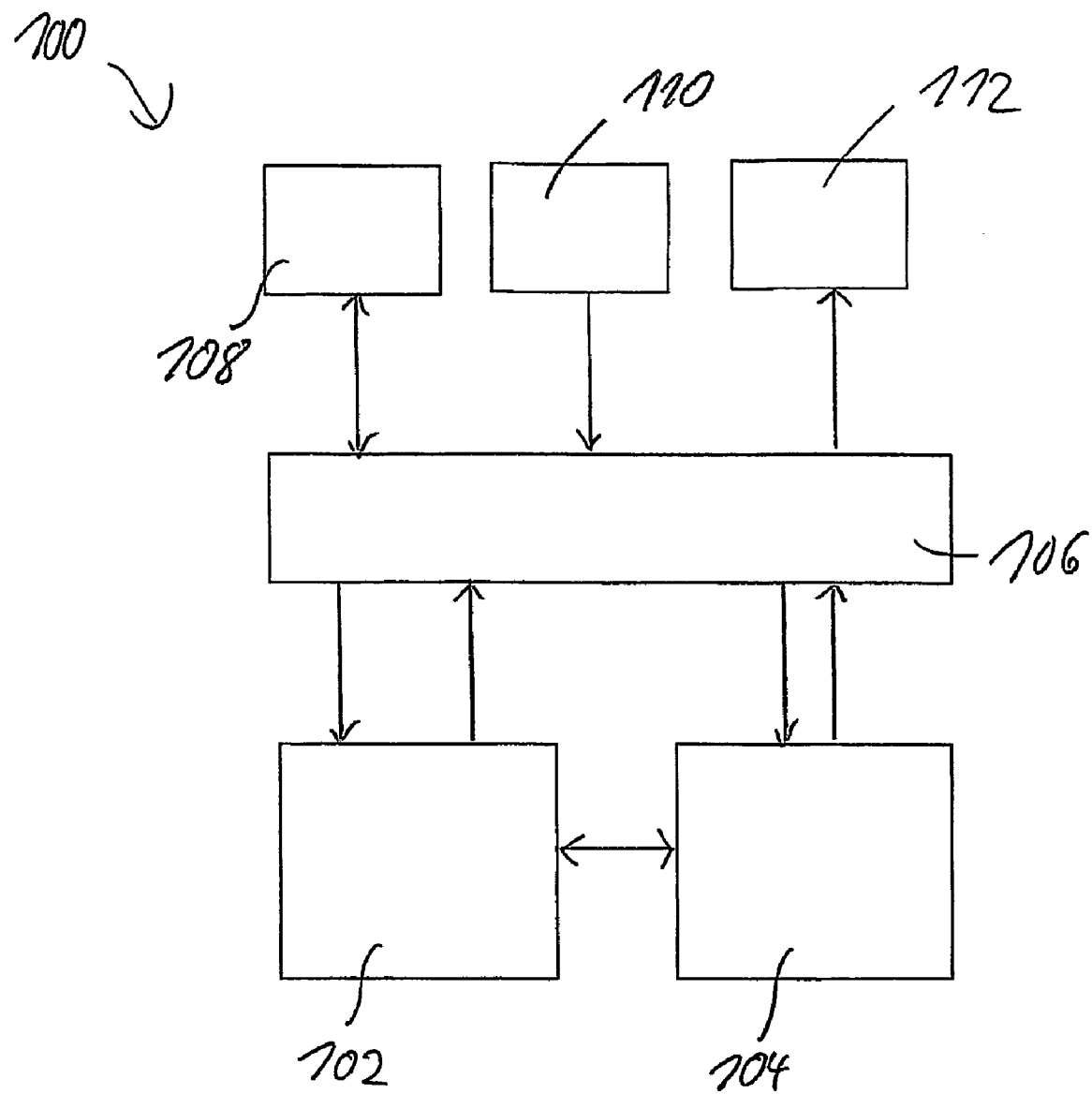
FIG. 24 shows schematically the basic structure of a quantification apparatus, which might be used for performing the method according to the invention.

Further, and as shown in FIG. 24, the invention refers to and, according to the first, more general, aspect, provides an apparatus 100 for quantification of at least one target nucleic acid in a test sample or in a plurality of test samples in accordance with the method of the invention. The apparatus according to the invention comprises:
  an amplification unit 102 for effecting a nucleic acid amplification process with respect to at least one test sample;

a detection unit 104 for measuring, at a plurality of different times during said nucleic acid amplification process effected by said amplification unit, at least two signals being related to a respective nucleic acid which is amplified in the amplification process, the detection mechanism being adapted to independently measure at least one first signal related only to a first nucleic acid and at least one second signal related only to a second nucleic acid or to measure at least one first signal and at least one second signal from which first data related only to a first nucleic acid and second data related only to a second nucleic can be calculated;

a controller 106 in communication with said amplification unit and said detection mechanism;

wherein said controller is adapted or programmed to perform the steps of controlling the amplification unit 102 to effect an amplification with respect to at least one respective test sample;

controlling the detection unit 104 to directly or indirectly measure the amount of amplification product or a quantity indicating the amount of amplification product for at least two different nucleic acids, namely with respect to at least one first nucleic acid und with respect to at least one second nucleic acid;

determining a characteristic value of said progress parameter for said first nucleic acid on basis of measurement results related to the amount of amplification product for said first nucleic acid;

determining a characteristic value of said progress parameter also for said second nucleic acid on basis of measurement results related to the amount of amplification product for said second nucleic acid;

quantifying the original amount of target nucleic acid in said test sample according to a predetermined quantification scheme, said quantification scheme provides for the quantification of the original amount of target nucleic acid in said test sample on basis of the characteristic value for said target nucleic acid, the characteristic value for said control nucleic acid and associated reference data;

providing quantification data that include said original amount of first nucleic acid to represent the original amount of target nucleic in said test sample.

With reference to the above second aspect of the invention, said controller, according to the invention, is adapted or programmed to perform the steps of:

bb) controlling the amplification unit 102 to effect an amplification with respect to at least one respective test sample;

cc) controlling the detection unit 104 to directly or indirectly measure the amount of amplification product or a quantity indicating the amount of amplification product for at least two different nucleic acids, namely with respect to at least one first nucleic acid und with respect to at least one second nucleic acid;

dd) determining a characteristic value of said progress parameter for said first nucleic acid on basis of measurement results related to the amount of amplification product for said first nucleic acid;

ee) if certain pre-defined conditions referring to the measured amount of amplification product for said second nucleic acid apply, determining a characteristic value of said progress parameter also for said second nucleic acid on basis of measurement results related to the amount of amplification product for said second nucleic acid;

ff) selecting between a plurality of quantification schemes according to at least one predefined selection criterion, said selection being effected directly or indirectly on basis of at least one of said measurement results related to the amount of amplification product for said first nucleic acid, measurement results related to the amount of amplification product for said second nucleic acid and said characteristic value or values, wherein at least one quantification scheme of a first type provides for a quantification of the original amount of first nucleic acid in said test sample on basis of the characteristic value for said first nucleic acid, the characteristic value for said second nucleic add and associated reference data, wherein at least one quantification scheme of a second type provides for a quantification of the original amount of first nucleic acid in said test sample on basis of the characteristic value for said first nucleic acid and associated reference data without reference to any characteristic value for said second nucleic acid, gg) quantifying the original amount of first nucleic acid in said test sample according to the selected quantification scheme on basis of at least the characteristic value determined for said first nucleic acid, jj) providing quantification data which include said original amount of first nucleic acid to represent the original amount of target nucleic in said test sample.

Said controller further can be adapted or programmed to perform steps b) to j) in accordance with the methods of the invention or/and to perform additional steps in accordance with the methods of the invention.

The invention further refers to and, according to the first, more general, aspect, provides a program of instructions executable by an apparatus 100 for quantification of at least one target nucleic acid in a test sample or in a plurality of test samples, the apparatus comprising:

an amplification unit 102 for effecting a nucleic acid amplification process with respect to at least one test sample;

a detection mechanism 104 for measuring, at a plurality of different times during said nucleic acid amplification process effected by said amplification unit, at least two signals being related to a respective nucleic acid which is amplified in the amplification process, the detection mechanism being adapted to independently measure at least one first signal related only to a first nucleic acid and at least one second signal related only to a second nucleic acid or to measure at least one first signal and at least one second signal from which first data related only to a first nucleic acid and second data related only to a second nucleic can be calculated;

a controller 106 in communication with said amplification unit and said detection mechanism;

wherein said controller in response to said instructions performs the steps of:

controlling the amplification unit to effect an amplification with respect to at least one respective test sample;

controlling the detection unit to directly or indirectly measure the amount of amplification product or a quantity indicating the amount of amplification product for at least two different nucleic acids, namely with respect to at least one first nucleic acid und with respect to at least one second nucleic acid;

determining a characteristic value of said progress parameter for said first nucleic acid on basis of measurement results related to the amount of amplification product for said first nucleic acid;

determining a characteristic value of said progress parameter also for said second nucleic acid on basis of measurement results related to the amount of amplification product for said second nucleic acid;

quantification of the original amount of target nucleic acid in said test sample according to a predetermined quantification scheme, said quantification scheme provides for the quantification of the original amount of target nucleic acid in said test sample on basis of the characteristic value for said target nucleic acid, the characteristic value for said control nucleic acid and associated reference data;

providing quantification data that include said original amount of first nucleic acid to represent the original amount of target nucleic in said test sample.

With respect to the above second aspect of the invention, said controller in response to said instructions, according to the methods of the invention, performs the steps of:

bb) controlling the amplification unit 102 to effect an amplification with respect to at least one respective test sample;

cc) controlling the detection unit 106 to directly or indirectly measure the amount of amplification product or a quantity indicating the amount of amplification product for at least two different nucleic acids, namely with respect to at least one first nucleic acid und with respect to at least one second nucleic acid;

dd) determining a characteristic value of said progress parameter for said first nucleic acid on basis of measurement results related to the amount of amplification product for said first nucleic acid;

ee) if certain predefined conditions referring to the measured amount of amplification product for said second nucleic acid apply, determining a characteristic value of said progress parameter also for said second nucleic acid on basis of measurement results related to the amount of amplification product for said second nucleic acid;

ff) selecting between a plurality of quantification schemes according to at least one predefined selection criterion, said selection being effected directly or indirectly on basis of at least one of said measurement results related to the amount of amplification product for said first nucleic acid, measurement results related to the amount of amplification product for said second nucleic acid and said characteristic value or values, wherein at least one quantification scheme of a first type provides for a quantification of the original amount of first nucleic acid in said test sample on basis of the characteristic value for said first nucleic acid, the characteristic value for said second nucleic acid and associated reference data, wherein at least one quantification scheme of a second type provides for a quantification of the original amount of first nucleic acid in said test sample on basis of the characteristic value for said first nucleic acid and associated reference data without reference to any characteristic value for said second nucleic acid, gg) quantification of the original amount of first nucleic acid in said test sample according to the selected quantification scheme on basis of at least the characteristic value determined for said first nucleic acid, jj) providing quantification data which include said original amount of first nucleic acid to represent the original amount of target nucleic in said test sample.

Said controller 106, in response to said instructions, can perform steps bb) to jj) in accordance with one of the methods of the invention.

Further, the invention provides a computer program product embodying the program. The computer program product can be in the form of a computer readable medium carrying said program of instructions.

Further, the invention provides a server computer system storing the program for downloading via a communication link, possibly via internet.

In the following, exemplary embodiments of the invention are presented.

Some of the illustration examples included herein refer specifically to a COBAS AmpliPrep™/COBAS TaqMan® HBV Test manufactured by Roche Molecular Systems, Inc., USA. However, this particular test serves only as an example, and the invention can be applied to any other quantification test. Accordingly, the following background information concerning the HBV Test indicates, for example, how a certain quantification test directed to a particular DNA might be implemented in the context of the present invention. Of course, other instruments, other amplification mixtures, other detection methods can be used. Accordingly, the COBAS AmpliPrep™/COBAS TaqMan® HBV Test has to be considered to be only a non-limiting example which is used herein only for illustration purposes.

The COBAS AmpliPrep™/COBAS TaqMan® HBV Test is an in vitro nucleic acid amplification test for the quantitation of Hepatitis B Virus (HBV) DNA in human serum or plasma, using the COBAS AmpliPrep™ instrument for specimen processing and the COBAS TaqMan™ Analyzer for amplification and detection. The test can quantitate HBV DNA over a wide range of concentrations. Specimen preparation is automated using the COBAS AmpliPrep™ Instrument, and amplification and detection are automated using the COBAS TaqMan™ or the COBAS TaqMan 48™ Analyzer.

The COBAS AmpliPrep™/COBAS TaqMan® HBV Test is based on simultaneous PCR amplification of target DNA and detection of cleaved dual-labeled oligonucleotide detection probe that is specific to the target.

The COBAS AmpliPrep™/COBAS TaqMan® HBV Test quantitates HBV viral DNA by utilizing a second target sequence (HBV Quantitation Standard, Internal Control, Internal Standard, IQS, QS) that is added to each test sample at a known concentration (known copy number). The HBV Quantitation Standard is a non-infectious DNA construct, containing fragments of HBV sequences with primer binding regions identical to those of the HBV target sequence. The HBV Quantitation Standard contains HBV primer binding regions and generates an amplification product of the same length and base composition as the HBV target DNA. The detection probe binding region of the HBV Quantitation Standard has been modified with respect to the detection probe binding region of the HBV Quantitation Standard. These unique probe binding regions allow the HBV Quantitation Standard amplicon to be distinguished from HBV. The HBV Quantitation Standard compensates for effects of inhibition and controls the preparation and amplification processes to allow the accurate quantitation of HBV DNA in each sample.

The COBAS AmpliPrep™/COBAS TaqMan® HBV Test permits automated sample preparation followed by automated PCR amplification, and detection of HBV target DNA and HBV Quantitation Standard (Internal Control). The Master Mix reagent contains primer pairs and probes specific for both HBV DNA and HBV Quantitation Standard DNA. The detection of amplified DNA is performed using a target-specific and a Quantitation Standard-specific dual labeled oligonucleotide probe that permits independent identification of HBV amplicon and HBV Quantitation Standard amplicon. The COBAS TaqMan™ Analyzer calculates the HBV DNA concentration in the test samples by comparing the HBV signal to the HBV Quantitation Standard signal for each sample and control.

Processed samples are added to the amplification mixture in amplification tubes (K-tubes) in which PCR amplification occurs. The Thermal Cycler in the COBAS TaqMan™/TaqMan 48™ Analyzer heats the reaction mixture to denature the double stranded DNAs and expose the specific primer target sequences on the HBV circular DNA genome and the HBV Quantitation Standard DNA. As the mixture cools, the primers anneal to the respective target DNA sequence of the HBV target DNA and to the HBV Quantitation Standard DNA. Under appropriate conditions the DNA polymerase extends the annealed primers along the target template to produce double-stranded DNA molecule termed an amplicon.

The COBAS TaqMan™/TaqMan 48™ Analyzer automatically repeats this process for a designated number of cycles, with each cycle intended to double the amount of amplicon DNA. The required number of cycles is preprogrammed into the COBAS TaqMan™/TaqMan 48™ Analyzer. Amplification occurs only in the region of the HBV genome between the primers; the entire HBV genome is not amplified.

The COBAS AmpliPrep™/COBAS TaqMan® HBV Test utilizes state of the art PCR technology, including for example the probes and detection formats used in the TaqMan™ instrument. The use of dual-labelled fluorescent probes allows for real-time detection of PCR product accumulation by monitoring of the emission intensity of fluorescent reporter dyes released during the amplification process. The probes consist of an HBV and HBV Quantitation Standard-specific oligonucleotide probes with a reporter dye and a quencher dye. In the COBAS AmpliPrep™/COBAS TaqMan® HBV Test, the HBV and HBV Quantitation Standard probes are labeled with different fluorescent reporter dyes. When the probes are intact, the reporter fluorescence is suppressed by the proximity of the quencher dye due to Förster-type energy transfer effects. During PCR, the probe hybridizes to a target sequence and is cleaved by the 5'->3' nuclease activity of the DNA polymerase. Once the reporter and quencher dyes are released and separated, quenching no longer occurs, and the fluorescent activity of the reporter dye is increased. The amplification of HBV DNA and HBV Quantitation Standard DNA are measured independently at different wavelengths. During the annealing phase of the PCR on the COBAS TaqMan™ Analyzer, the samples are illuminated and excited by filtered light and filtered emission fluorescence data are collected for each sample. This process is repeated for a designated number of cycles, each cycle effectively increasing the emission intensity of the individual reporter dyes, permitting independent identification of HBV and HBV Quantitation Standard DNA. The PCR cycle where a growth curve starts exponential growth is related to the amount of starting material at the beginning of the PCR.

The PCR used is quantitative over a wide dynamic range since the monitoring of amplicon is performed during the exponential phase of growth. The higher the HBV concentration of a sample, the earlier the fluorescence of the reporter dye of the HBV probe rises above the baseline fluorescence level. Since the amount of HBV Quantitation Standard (QS) DNA is constant between all samples, the fluorescence of the reporter dye of the HBV QS probe should appear at or near the same cycle for all samples. In case where the QS fluorescence is affected, the concentration is adjusted accordingly. The appearance of a specific fluorescent signal is reported as a critical threshold value (ct), and in the following is also denoted as an "elbow value" nT or $ct_T$, referring to the target (in the present example the HBV target DNA) and as an "elbow value" nQ or $ct_{QS}$, referring to the internal control (in the present example the HBV quantification standard DNA). The ct is defined as the fractional cycle number where reporter dye fluorescence exceeds a predetermined threshold, and starts the beginning of an exponential growth phase of this signal. A higher ct value indicates a lower concentration of initial target material Target growth curves for a dilution series spanning a desired range can be obtained. As shown in FIGS. 13A, 13C, 15A and 15C, as the concentration of the sample increases the growth curves shift to earlier cycles. Therefore the leftmost growth curve corresponds to the highest target concentration level whereas the rightmost growth curve corresponds to the lowest target concentration level. For each growth curve the fluorescence values at every cycle are normalized. The fractional ct value is calculated where the fluorescence signal crosses a predefined fluorescence level.

Lot-specific calibration constants provided with the COBAS AmpliPrep™/COBAS TaqMan® HBV Test are used to calculate the concentration value for the initial sample based upon the HBV DNA and HBV Quantitation Standard DNA ct values.

As exemplified in the COBAS AmpliPrep™/COBAS TaqMan® HBV Test, differences between the ct values of the HBV DNA and HBV quantification standard DNA can be calculated, and the concentration value for the initial sample can be calculated on basis of these difference values and the lot-specific calibration constants.

According to one embodiment, the determination of the lot-specific calibration constants is considered part of the method provided by the invention. The calibration constants can be determined by quantitating a dilution series of target DNA (e.g. HBV DNA), wherein each sample of the dilution series includes the same known concentration of the internal control (e.g. HBV quantitation standard) which is also included in the respective test (e.g. COBAS AmpliPrep™/COBAS TaqMan® HBV Test). According to the terminology used in the field, this calibration is effected on basis of an "external standard".

It should be added that it is advantageous but generally not necessary that the internal control (internal quantification standard) on the one hand and the target (see above example of HBV viral DNA) are similar with identical primer regions and amplification products of the same length and base composition. One might even use different primers. However, using similar target and internal control sequences and identical primers has the advantage that the amplification efficiencies for both amplification reactions occurring simultaneously should be identical, or nearly identical.

In the following, examples referring to the calibration of a respective quantification test and the calibration part of a corresponding method provided by the invention are presented.

The calibration of a given quantification test which uses an internal control can, according to one embodiment of the invention, be effected for example as illustrated in FIGS. 1a and 1b. In a first step (step A-1) a dilution series of samples is provided which each include a respective copy number $T_{0i}$ of the target nucleic acid (referring to the above example e.g. HBV DNA) and the same number of internal control or quantification standard nucleic acid (referring to the above example e.g. HBV quantification standard DNA constructs). The dilution series includes S individual samples.

Using appropriate instrumentation, e.g. the COBAS TaqMan™ Analyzer, the samples are amplified by PCR-amplification over P cycles (step A-2). During the amplification, the fluorescence intensities indicating the PCR product accumulation are measured. This can be done on basis of probes and detection formats as used in the TaqMan™ instrument or on basis of other means known in the art. There can be crosstalk between fluorescence signals due to an overlap of the fluorescence emission spectra and receiving bandwidth of the fluorescence detector associated to another PCR product. This crosstalk can be corrected by effecting a multicomponent analysis. For example, a so-called crosstalk calibration on basis of color standards can be effected to provide an essay-specific crosstalk matrix which can be used to convert a filter-reading vector obtained from the measurements into a crosstalk-free fluorescent intensity vector.

On basis of the measured fluorescence intensities for each sample a target growth curve T and a control growth curve Q are obtained (step A-3).

If desired, pre-checks and corrections can be effected with respect to the growth curves, for example to eliminate artifacts, to compensate for instrumental fluctuations and the like. The growth curves can be normalized, for example by dividing each growth curve raw fluorescence value by the intercept value of the growth curve base line with the ordinate. FIG. 2 shows a corresponding example.

On basis of the growth curves, for example, on basis of the normalized growth curves, a respective characteristic value indicating a certain momentarily status of the amplification is determined (step A-4). In the present example, so-called "elbow values" nT for the target growth curves and nQ for the control growth curves are determined which correspond to a fractional cycle number at which the respective growth curve crosses an arbitrary signal value ASV (FIG. 2). To obtain a fractional cycle number an appropriate interpolation of the growth curve between growth curve points obtained from the measurement can be effected.

Generally, for each sample i a target elbow value $nT_i$ and a control elbow value $nQ_i$ is obtained (step A-5). However, for high initial target concentrations $T_0$ it might happen that the PCR amplification with respect to the internal control gives no characteristic growth curve within the cycles 1 to P, so that no control elbow value can be obtained. Such a dropout of the control growth curve is caused by competitive effects between the target and the internal control. The method might be implemented appropriately to take into account possible dropouts of the control growth curves. In the following steps only those samples should be taken into account for which appropriate target elbow values $nC_i$ and appropriate control elbow values $nQ_i$ were obtained. Corresponding checks of the elbow values, which were determined, can be implemented on basis of theoretical considerations, in particular the dynamics of the PCR amplification.

For all appropriate pairs $nT_i$, $nQ_i$ a respective elbow difference $\Delta n_i = nQ_i - nT_i$ is calculated (step A-6). Accordingly, for each sample of the dilution series or, in case of control growth curve dropout, for each sample of a subset of the dilution series a value pair $(T_{0i}, \Delta n_i)$ is obtained (step A-7) which relates the respective initial target concentration $T_{0i}$ to the elbow difference $\Delta n_i$ determined for the respective sample i.

These value pairs allow the calibration of the respective quantification test (step A-8). For example, a theoretical calibration formula derived from the exponential amplification function can be used. According to the example considered here, a quantification formula (quantitation equation) of second order is used which was shown to accurately represent the relationships between the target and control growth curves. This second order polynomial equation can sufficiently take into account competitive effects in the co-amplification (e.g. primer competition). By fitting the calibration formula to the data pairs $(T_{0i}, \Delta n_i)$ for example by the RMS method or the KRC method, the appropriate parameters a, b and c of the calibration formula shown in FIG. 1b can be obtained, which serve as calibration constants. Further, the amplification efficiency $\epsilon$ and a proportionality constant f between the amplification of the target and the amplification of the internal control can be obtained.

Figures 3, 4, 5:
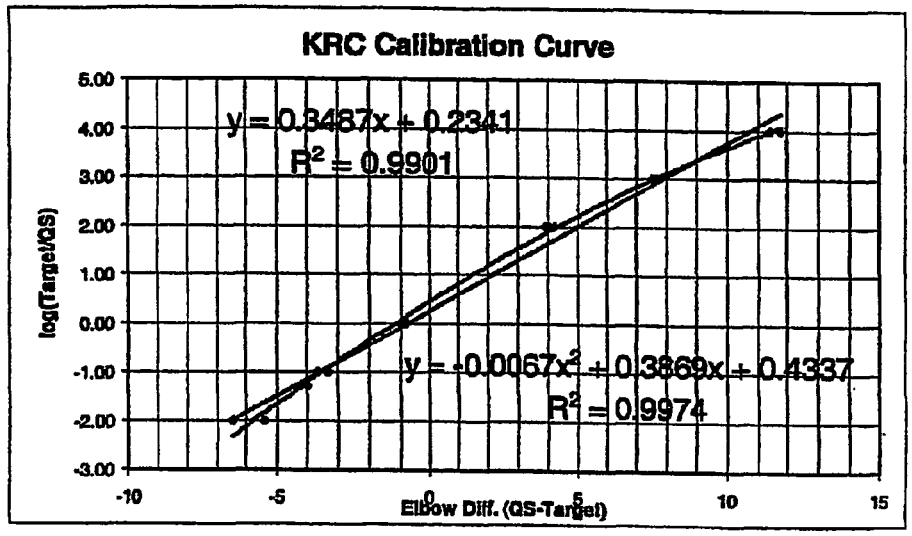
FIGS. 3 to 8 show diagrams and plots including numerical examples for a calibration effected in agreement with FIGS. 1a, 1b.

The calibration can be further illustrated on basis of numerical examples shown in FIGS. 3 to 8. FIG. 3 is a sheet of input data and amplification result data for 24 samples. Before the PCR amplification, each sample included the same copy number of internal control nucleic acids (1000 copies). In the second column the initial amount (copy number) of target nucleic acid for the respective sample is given. Columns 4 and 5 show the elbow value $n_{Qs}$ of the amplification of the internal control and the elbow value $n_T$ of the PCR amplification of the target. The difference between these elbow values is given in column 6.

FIG. 4 is a plot of the log(target input copy #/IQS input copy #) versus (elbow of IQS—elbow of target). Further, two calibration curves, one of first order and the other of second order, are plotted as fitted to the data points obtained from the amplification. For the fit, the KRC method was used. The slope and intercept of the linear fit according to the KRC method yields the co-amplification efficiency $\epsilon$ and the constant of proportionality f.

To estimate the degree of fit one can back-calculate the titers using the regression data. FIG. 5 shows, in comparison with the respective actual target input copy number, such back calculations on basis of the linear and polynomial regression data, as well as on basis of the exponential amplification formula using values for f and $\epsilon$ obtained from the fit.

Figure 6:
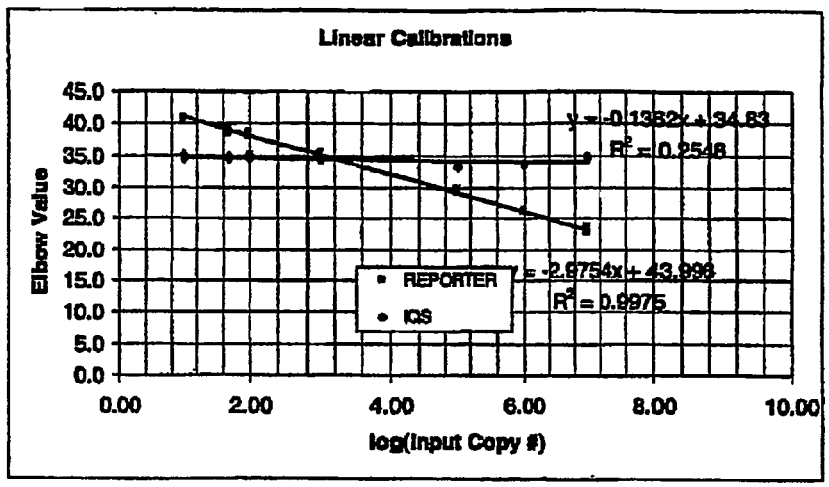
Figure 7:
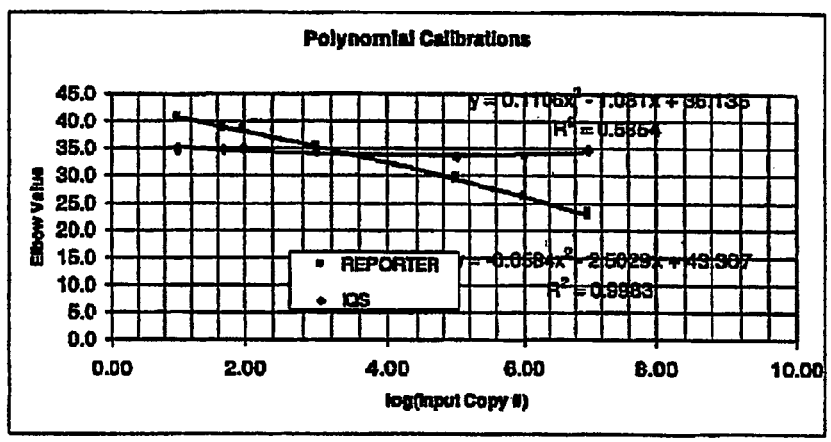

It is possible to additionally fit the target elbow values (reporter elbow values) on the one hand and the internal control (IQS) elbow values on the other hand independently of each other to respective calibration formula. Corresponding examples are shown in FIGS. 6 and 7. According to one embodiment of the method, such calibration data are used for the quantification of samples which show a dropout of the control growth curve or a degenerated control growth curve, so that no appropriate control elbow value or no control elbow value at all could be determined.

Figure 8:
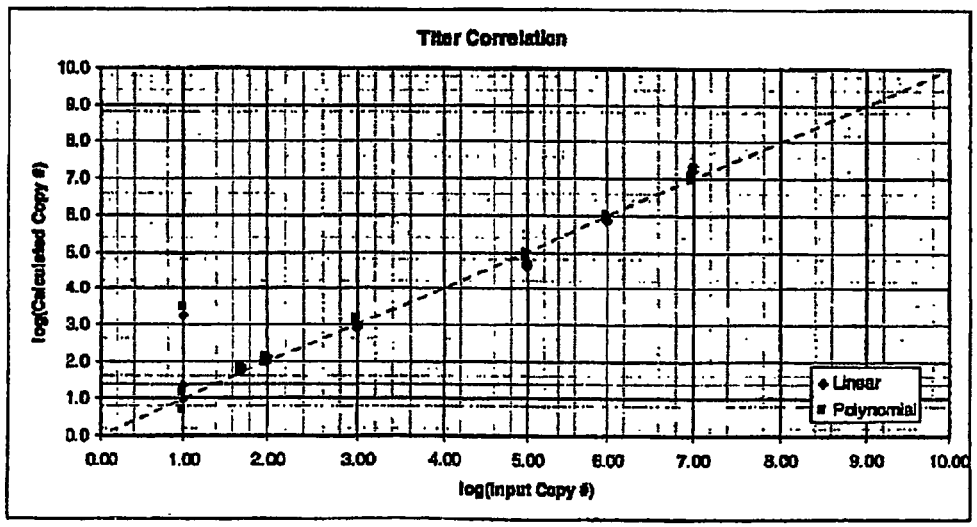

FIG. 8 shows the back calculation results on basis of the regression fits correlated to the actual data.

It has already been mentioned that for quantification of samples having high initial target concentrations an additional calibration can be effected. It is referred to FIG. 9. According to a first variant denoted as B1 the initial target copy numbers (or concentrations) $T_{0i}$ and the respective target elbow values $nT_i$ of the samples used for the calibration according to FIGS. 1a and 1b are accessed (step B2-2) and used (step B1-2) to determine calibration constants A, B, C on basis of an appropriate calibration formula, e.g. second order polynomial equation. Since the control elbow values are not needed, the amplification results for all samples can be used, even if there have been control growth curve dropouts. Beside the calibration constants, the amplification efficiency can be provided (step B1-3) on basis of a corresponding fit of the calibration formula to the data points.

According to a more simple approach, only the amplification result for a selected sample j is accessed (step B2) and used which has an elbow value $nT_j$ corresponding approximately to a predefined reference value $nT_{ref}$. The predefined reference value $nT_{ref}$ corresponds to a relatively high initial target concentration (copy number), leading to a relatively low elbow value, so that for this target concentration or for somewhat higher target concentrations there is a higher probability of control growth curve dropouts. The value pair $(T_{0j},$ $nT_j$) itself can be used as calibration constant on basis of the exponential amplification function, possibly together with a theoretical amplification efficiency or with the amplification efficiency obtained from the calibration referred to in the foregoing.

It should be added that, in agreement with the examples discussed in the foregoing, elbow values or threshold values are determined on basis of the growth curves. However, instead of such elbow or threshold values one may use other characteristic values, for example determined on basis of the first, second or nth derivatives of a respective growth curve.

Figure 10B:
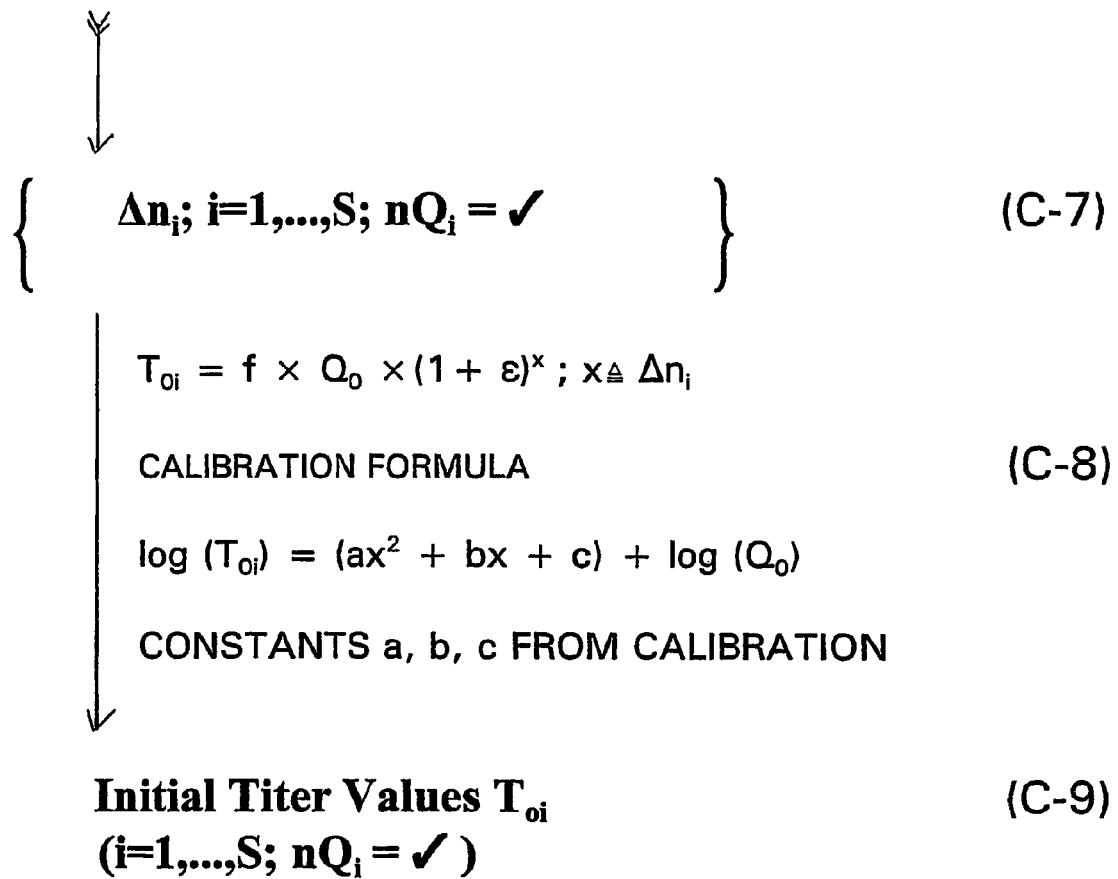
Figure 73:
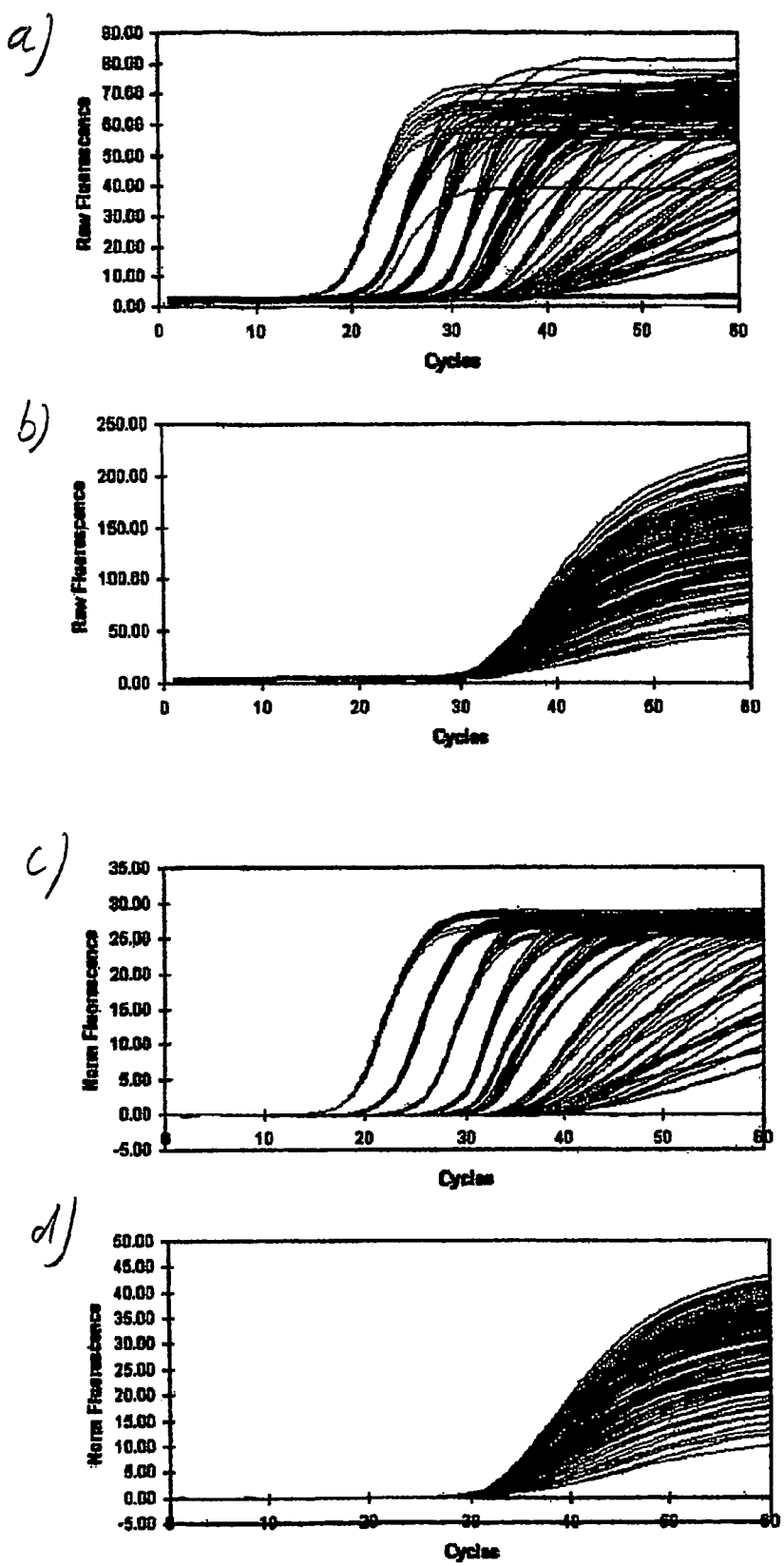

With reference to FIG. 10a and FIG. 10b the quantification of samples containing an unknown target titer $T_0$ can be effected as follows. After providing one sample or a set of samples with unknown target titer $T_{0i}$ and equal known control titer $Q_0$ as used in the calibration (step C-1), the PCR amplification with measurement of the fluorescence intensity is effected as in the method part referring to the calibration (step C-2). If necessary, crosstalk correction is effected. From the amplification a respective target growth curve $T_i$ is obtained and generally also a control growth curve $Q_i$ (step C-3). After effecting pre-checks and corrections (if desired), the data are normalized and elbow values for the growth curves are determined (step C-4). Generally, for each sample a target elbow value $nT_i$ and a control elbow value $nQ_i$ are obtained (step C-5). However, there might be a dropout of the control growth curve, if the initial target titer $T_0$ was relatively high. For such samples, only a target elbow value $nT_i$ is obtained. However, there is also the possibility that control elbow values $nQ_i$ occur which are not appropriate and have to be discarded.

After calculating the elbow differences $\Delta n_i$ (step C-6), the input values $\Delta n_i$ for the calibration formula are obtained (step C-7). On basis of the calibration formula and the constants a, b, c obtained from the calibration the initial titer values $T_{0i}$ can be calculated (steps C-8, C-9).

For samples which showed a dropout in the control growth curve, so that no control elbow value could be determined, or for which an inappropriate control elbow value was obtained, the initial titer $T_{0i}$ can be obtained on basis of the respective target elbow value $nT_i$ using an appropriate calibration formula and associated calibration data, e.g. the formula and data according to embodiments B1) and B2) of FIG. 9. It is referred in this respect to the process according to steps D1-1, D1-2 and D1-3 and according to steps D2-1, D2-2 and D2-3 as illustrated in FIG. 11a and FIG. 11b.

In the following, the invention is further exemplified on basis of a particular example, namely the COBAS AmpliPrep™/COBAS TaqMan® HBV Test referred to in the foregoing. FIG. 12 shows the print on the packet of the COBAS CAP/CTM HBV Test kit used. This test kit will be obtainable from Roche Molecular Systems, Inc., Branchburg, N.J. USA, or from Roche Diagnostics GmbH, Mannheim, Germany.

FIG. 13 shows growth curves for a dilution series of HBV plasmid target and internal controls obtained on basis of the HBV test according to FIG. 12. The dilution series of HBV plasmid is a series of 1e1 to 1e9 CTMU/ml target sequence and 5.0 e3 CTMU/ml internal control sequence. The unit CTMU refers to a so-called COBAS TaqMan™ unit. There is a calibration factor generally between 1 and 3 relating 1 CTMU/ml to a certain copy number/ml. In view of the merely illustrative purposes herein one might identify one CTMU as one copy for simplicity.

To the solution series two samples of WHO-EUROHEP-Standard including 1e4 CTMU/ml target were added for reference purposes.

FIG. 13a shows the unnormalized target growth curves, and FIG. 13b shows the unnormalized control growth curves. A normalization which removes the baseline offset leads to the target growth curves of FIG. 13c and the control growth curves of FIG. 13d.

Figure 14:
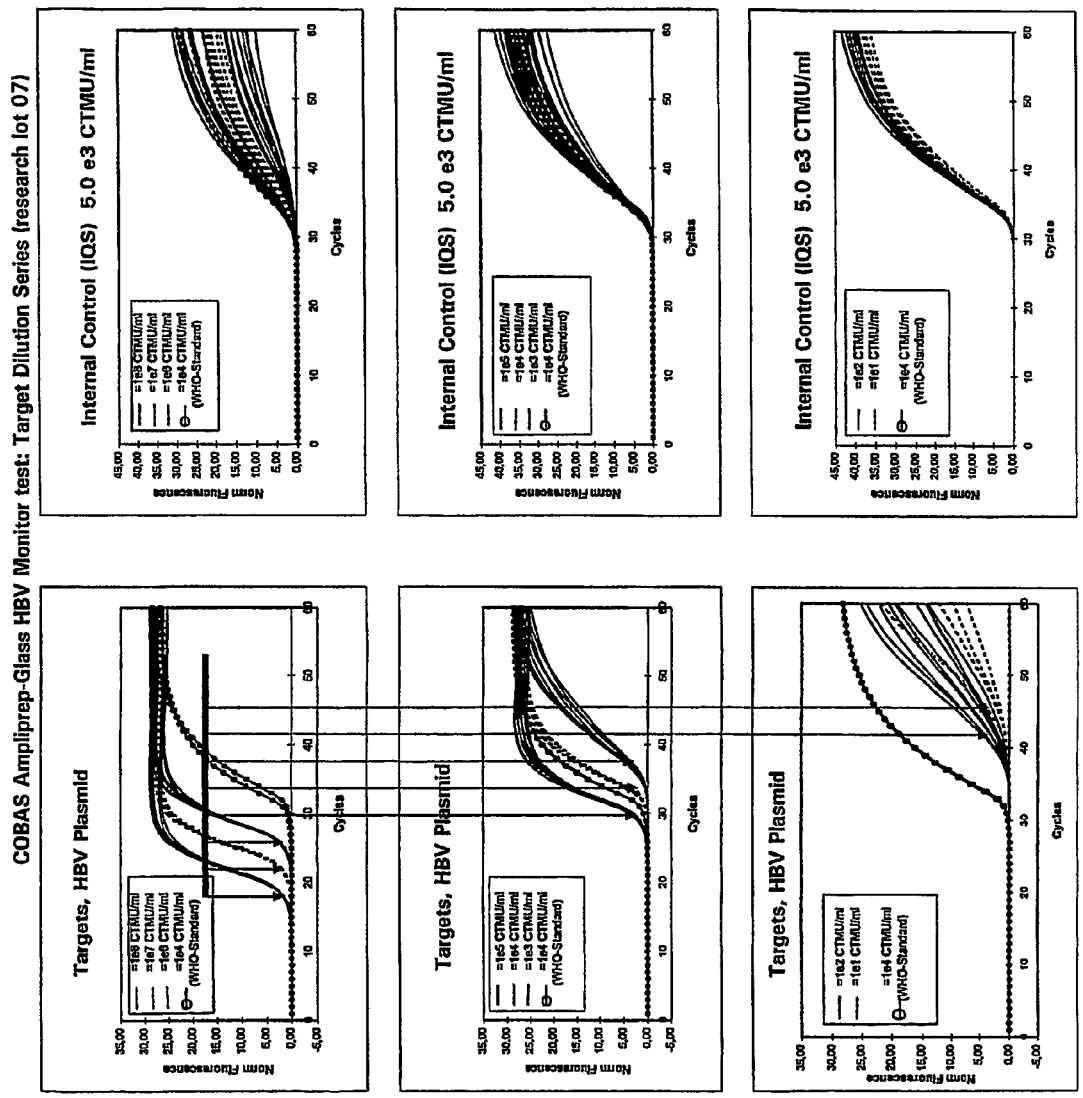
FIG. 14 indicates respective elbow values for the target growth curves of the example in FIG. 13.
Figure 75:
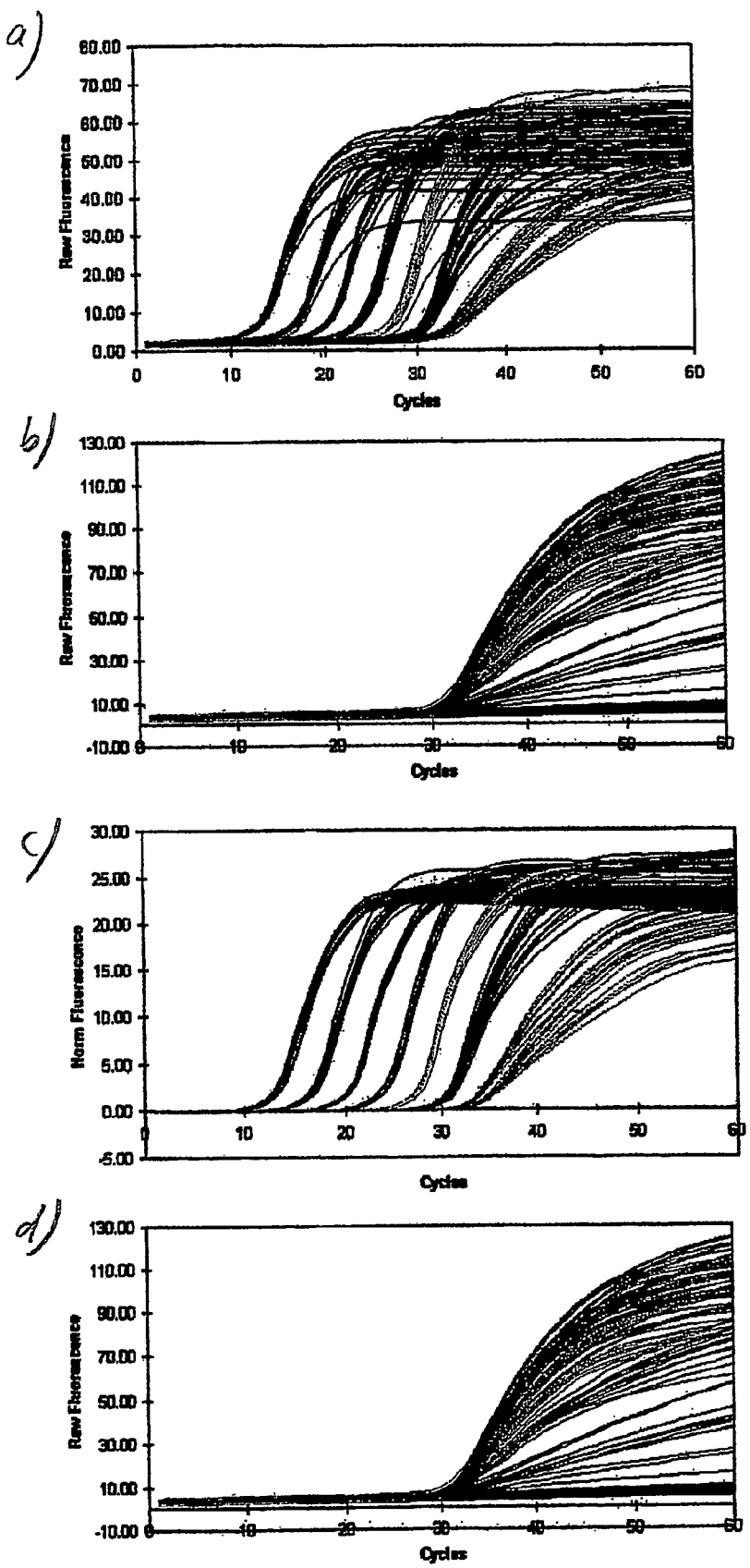

In the control growth curves, there is no internal control failure value (no dropout of a control growth curve) visible. Even for the highest concentrations of HBV plasmid (1e8 and 1e9) the growth curves of the internal control show a distinct growth and separate distinct from the baseline. Accordingly, a desired titer measurement range of for example about 5 decades is reached. In principle, it is sufficient to use the standard quantification on basis of the elbow differences. FIG. 14 indicates respective elbow values for the target growth curves. The elbow values for the control growth curves are not shown.

Figure 16:
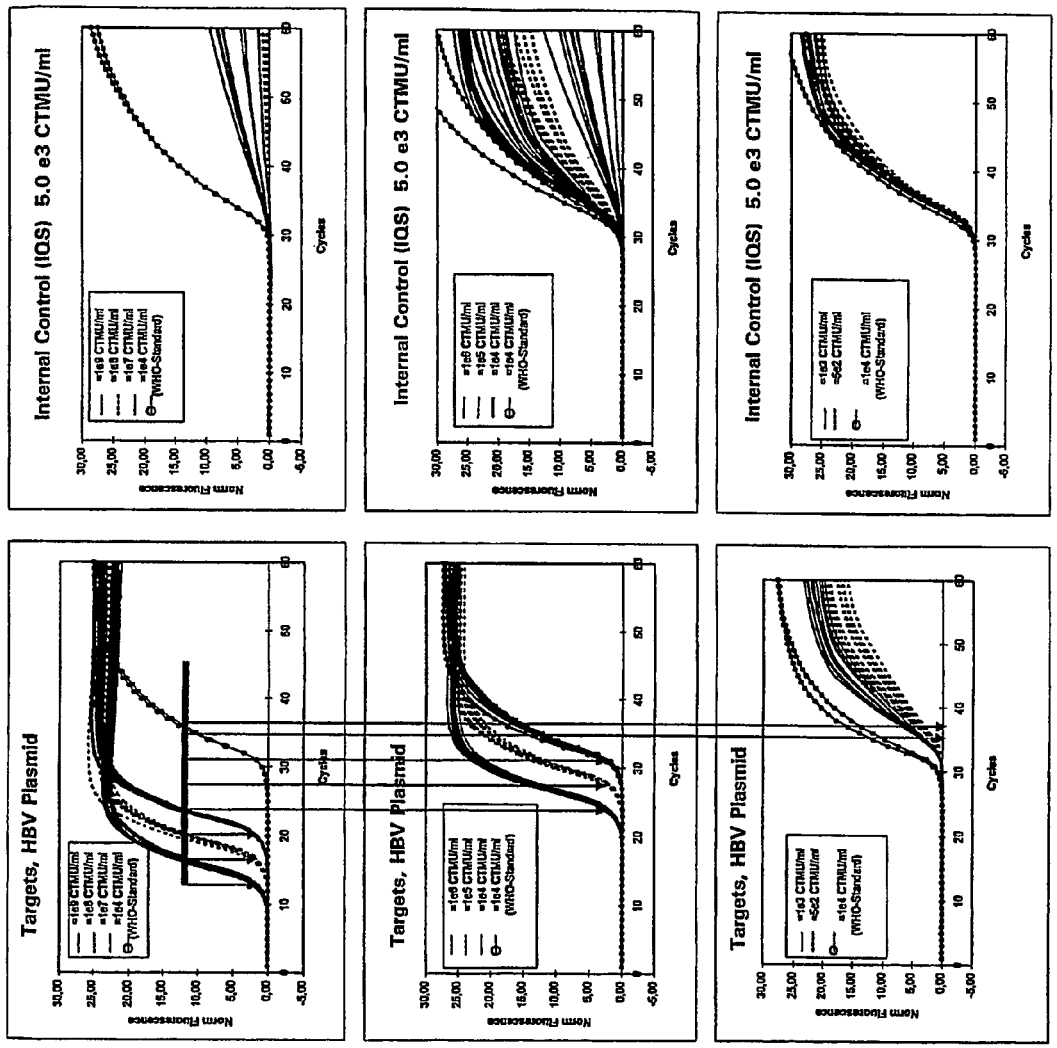
FIG. 16 indicates respective elbow values for the target growth curves of the example in FIG. 15.

The situation is different for another target dilution series ranging from 5e2 CTMU/ml to 1e9 CTMU/ml of target HBV plasmid, with 5.0 e3 CTMU/ml internal control, for which the unnormalized and normalized growth curves are shown in FIG. 15. In this dilution series the WHO-EUROHEP-Standard of 1e4 CTMU/ml was added (two samples). Although the target curves still show a nice and smooth dependence and reflect the concentrations as expected, the internal control suffers obviously from high target concentrations. At concentrations of 1e8 and higher very low internal control signals were obtained, so that the probability of a complete failure of the standard quantification on basis of elbow differences is dramatically increased. For some samples obviously no control elbow value can be determined, so that the standard quantification fails. FIG. 16 indicates respective elbow values for the target growth curves. The elbow values for the control growth curves are not shown.

In the following, embodiments and modifications of the calibration and quantification considered on basis of FIGS. 1 to 11 are presented. Formula F0 of FIG. 17a shows the standard titer calculation formula for COBAS TaqMan™ instrument growth curves using elbow value differences. Formula F0 can be written in a simplified format, with constants a, b, c for a fixed internal control copy number Q, for a fixed recovery r and for a fixed volume factor v, since it is not necessary to treat Q, r and v as parameters. Accordingly, the standard calibration formula already considered in the foregoing is obtained.

To avoid the use of inappropriate control elbow values, one may calculate the target titer directly from the elbow value $ct_T$ (denoted as nT in the foregoing) of the target growth curve, if the elbow value of the target is below a threshold value of for example 20. For the HBV test a target elbow value of 20 corresponds to about $5*10^6$ copies. For such relatively small target elbow values, formula F1 can be used in agreement with the "exceptional" quantification according to steps D2-1, D2-2 and D2-3. The high titer calculation function F1 assumes an exponential growth with amplification factor $AF=1+\epsilon=2$ per cycle. This is a somewhat idealistic assumption. It must be expected, that this approach generally overestimates the real growth and that a correction to an amplification factor smaller than 2 would improve the quality of high titer quantitation.

The values of $T_{ref}$ and $ct_{ref}$ (denoted as nQ in the foregoing) are reference values which are determined in a calibration procedure, for example on several instruments, for example, a high titer calibration B2. These values can be determined with respect to each reagent kit lot of a certain test. Within the calibration, basically two steps can be performed: i) quantification of the control reagent with reasonable position and accuracy and assignment to $T_{ref}$, ii) determination of an average ct which is found if the control reagent is applied to different instruments and assignment to $ct_{ref}$. The values for $T_{ref}$ and $ct_{ref}$ can be provided together with a respective reagent kit. For example, these values can be coded in bar code on reagent cassettes. When the reagent cassettes are loaded onto an amplification instrument (e.g. COBAS AmpliPrep™ Instrument) the $T_{ref}$ and $ct_{ref}$ data can be read by a bar code detector and transferred as input data to the control software of the instrument. Depending on the accuracy needed and the uniformity of the reagent kit lots lot specificity might not be necessary, so that it would be sufficient to determine $T_{ref}$ and $ct_{ref}$ test specifically.

One particular issue is that $T_{ref}$ should be found in a certain "ct range" (e.g. $19.3 < ct_{ref} < 20.7$). This corresponds to a log error of ±0.21. Further, $T_{ref}$ must be found in that "ct range" for all instruments. An alternative to this approach is the approach according to steps B1-1, B1-2 and B1-3 (calibration) and steps D1-1, D1-2 and D1-3 (quantification), using a second order calibration formula.

Instead of using a fixed theoretical amplification factor, one might use instead an amplification factor $AF=1+\epsilon$ per PCR circle which is derived from the calibration curve or data of the standard calibration. A corresponding formula is denoted as F2.

By looking at the standard calibration formula, the amplification factor AF is obtained for $\Delta ct = ct_{QS} - ct_T = 0$ ($AF = e^{b \ast \ln 10 b}$; b being the second parameter of the calibration coefficients). Accordingly, by using $AF = e^{b \ast \ln 10}$ instead of $AF=2$ in formula F2 it is possible to extract the amplification factor from the calibrated set of data and to use this factor also in the high target concentration region.

Figure 18:
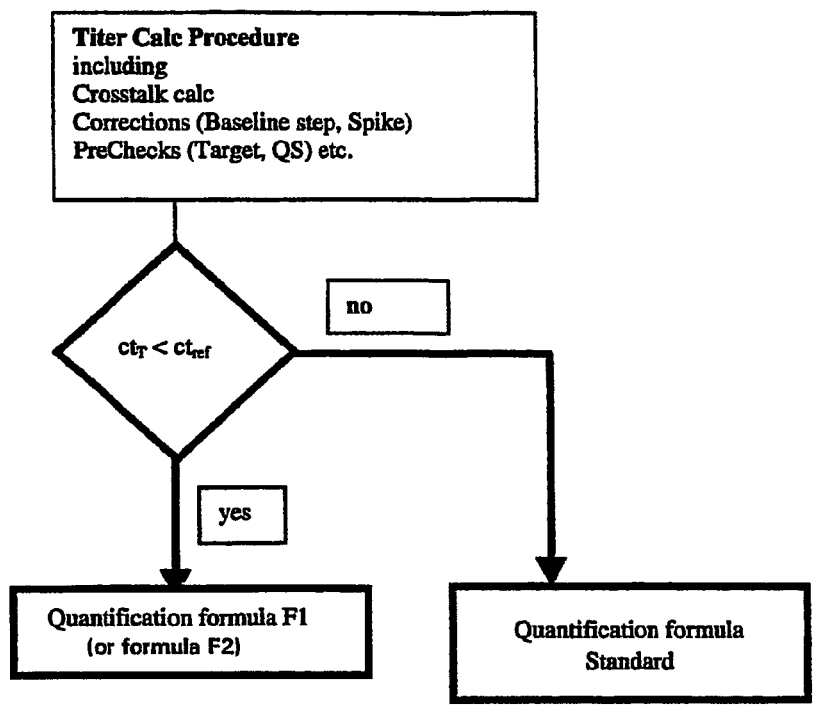
FIG. 18 is a flow chart showing one possibility how the selection between alternate quantification formulas can be effected.

FIG. 18 shows a flow chart part of a complete titer calculation algorithm in which, dependent on the value of the target elbow value $ct_T$ with respect to the reference elbow value $ct_{ref}$, either the standard quantification formula or the "exceptional" quantification formula F1 (or alternatively the "exceptional" quantification formula F2) is used.

Figure 19:
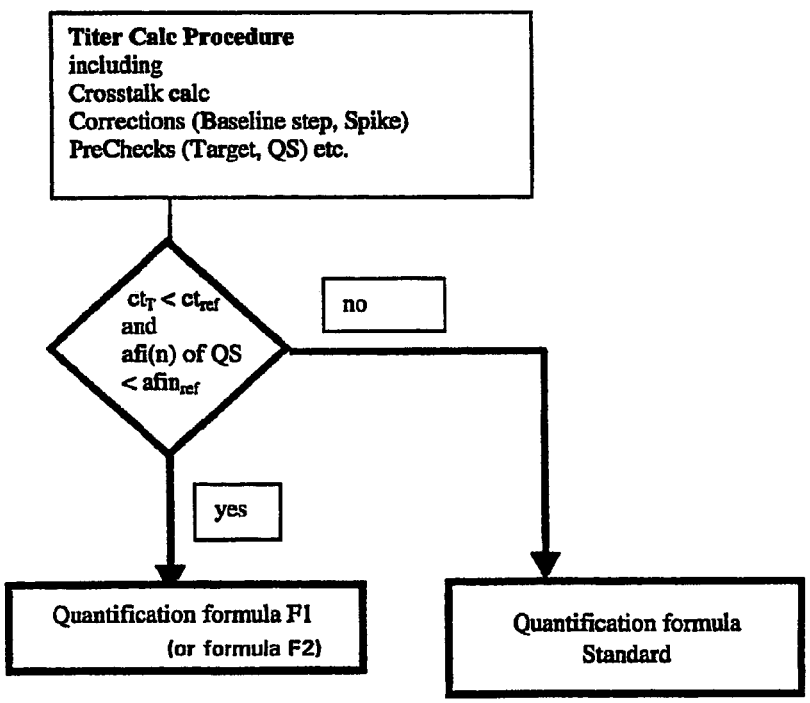
FIG. 19 is a flow chart showing another possibility how the selection between alternate quantification formulas can be effected.

A modification of this flow chart part is shown in FIG. 19. There are two conditions, which must be fulfilled for the exceptional quantification formula F1 or F2 to be applied. The additional condition is that the normalized internal control intensity value afi(n) after the last PCR amplification cycle does not exceed a certain threshold value afi(n)$_{ref}$. The threshold value afi(n)$_{ref}$ must be selected appropriately with respect to the normalizations effected. For the normalizations shown in FIGS. 13 to 16 a threshold value afi(n)$_{ref}$<2 means a very low plateau for the internal control QS. If these two conditions hold, the target titer is calculated directly from the ct of the target growth curve by using for example formula F1 or formula F2.

The modification according to FIG. 19 means that the exceptional quantification formula is only applied when the internal control curve fails completely or if this curve becomes very weak with a plateau value smaller than the threshold value. Accordingly, for growth curves as shown in FIG. 13 still the standard quantification formula would be used with respect to all samples.

Figure 20:
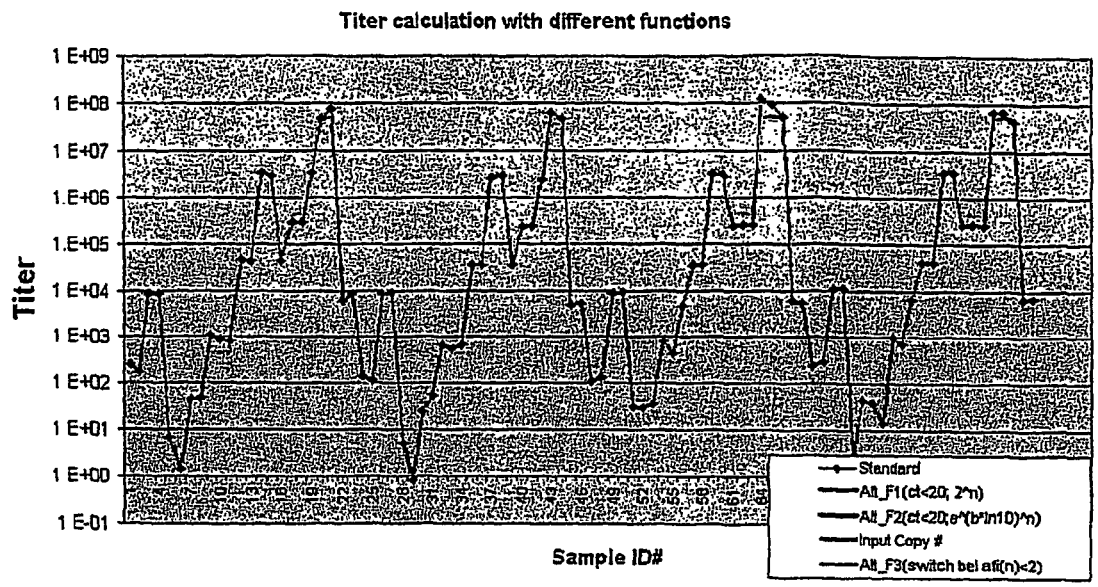
FIG. 20 shows the titer calculation results for the growth curve of FIG. 13.
Figure 21:
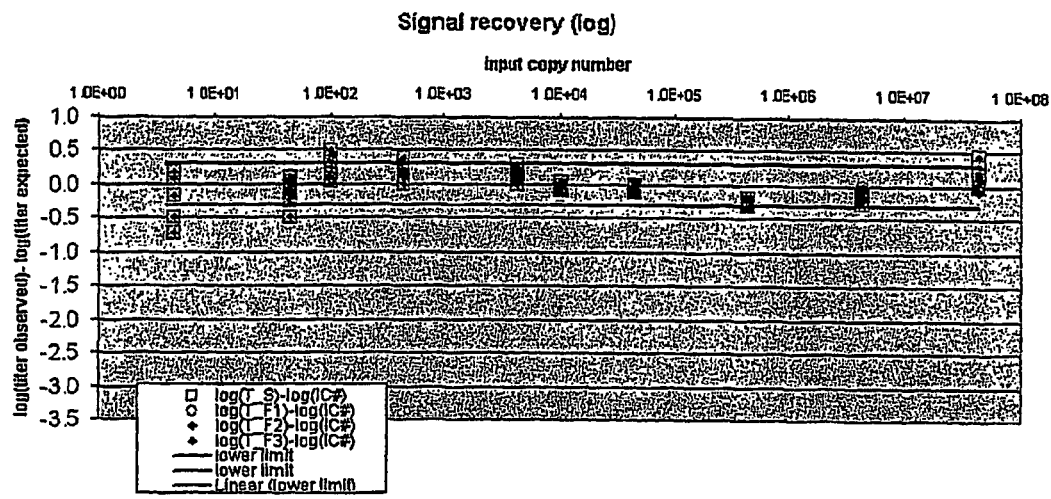
FIG. 21 shows the signal recovery results for the growth curve of FIG. 13.
Figure 22:
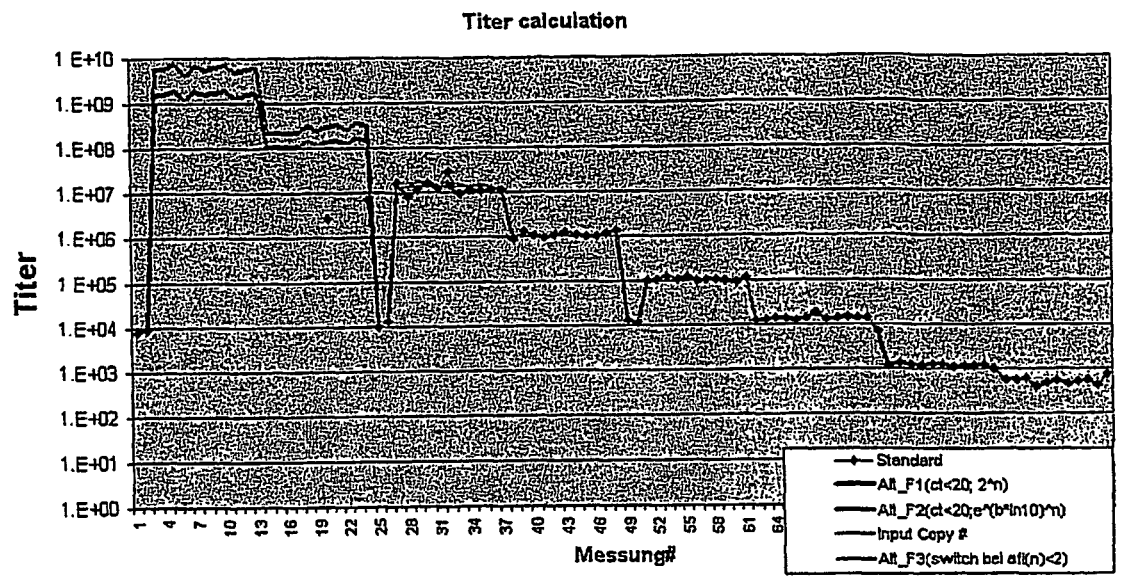
FIG. 22 shows the titer calculation results for the growth curve of FIG. 15.
Figure 23:
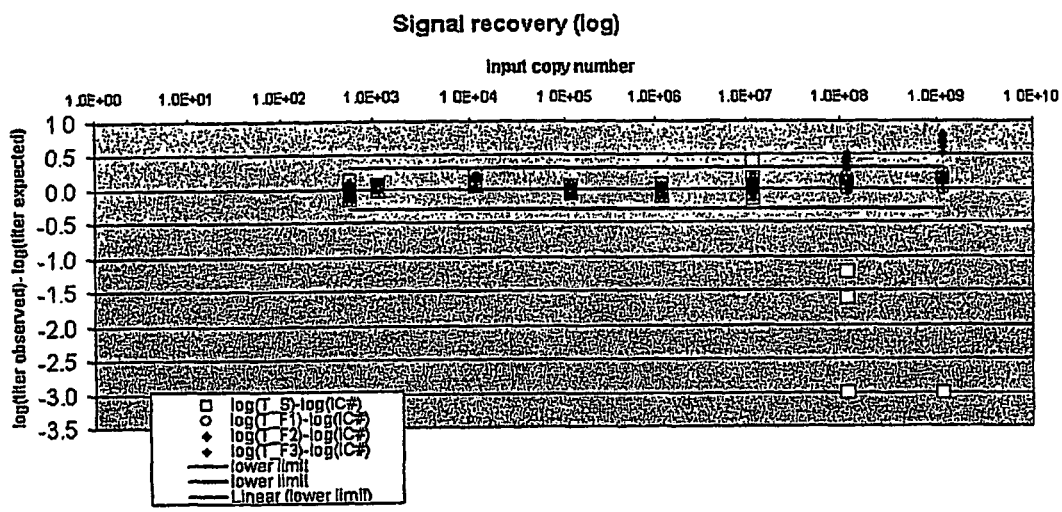
FIG. 23 shows the signal recovery results for the growth curve of FIG. 15.

An evaluation of the growth curves according to FIGS. 13 to 16 on basis of the standard quantification formula, the exceptional quantification formula F1, and the exceptional quantification formula F2 leads to the back calculation results of FIGS. 20 and 22 and the signal recovery results of FIGS. 21 and 23. Four quantification approaches were applied. The approach "standard" is based on the standard quantification formula only. The approach "F1" is based on the standard calibration formula and the exceptional quantification formula F1 together with the relevant flow chart part of FIG. 18. The approach "F2" is based on the standard quantification formula and the exceptional quantification formula F2, again in combination with the relevant flow chart part of FIG. 18. Further, the approach "F3" is again based on the standard quantification formula and the exceptional quantification formula F1, but not in combination with the relevant flow chart part shown in FIG. 18. Instead, the relevant flow chart part shown in FIG. 19 was used.

FIGS. 20 and 21 were obtained for the growth curve of FIG. 13. There are only small deviations between the quantification results obtained for the different approaches. The standard titer calculation works fine for the shown data because there is no failure in the internal control growth curves up to highest target concentrations. Further, the approach "F1" using the exceptional formula F1 in combination with the condition of FIG. 18 gives very good results. The calculation of all target yields above ~4e6 shows no visible deviation from the standard function. Indeed, it appears that the high yield values do not scatter as much as the standard function. This is reasonable because one can expect that the internal control signal shows an increased scatter at high target yields. This scatter cannot contribute in quantification formula F1.

Also, the exceptional quantification formula F2 used in combination with the condition of FIG. 18 (approach "F2") describes the titer excellently, like formula F1. The AF factor derived from the calibration curve (for the presented data: 1.95) is adequate for the high titer range.

Approach "F3" (formula F1 in combination with the condition of FIG. 19) gives the same results as the standard quantification formula since for the samples the afi(n) values of the internal control (QS) growth curve exceed the preset threshold value afi(n)$_{ref}$=2. Accordingly, the exceptional quantification formula was never applied.

The signal recoveries shown in FIG. 21 indicate, that a specification limit of log error ±0.3 represented by bars is not attained over the whole dynamical range and for all formulas. However, on the whole, reasonable performance is obtained, in particular for the standard quantification formula and formula F1.

FIGS. 22 and 23 are based on the amplification results of FIG. 15. Again, the approaches "standard", "F1", "F2", and "F3" as defined with respect to FIGS. 20 and 21 were used.

The standard quantification formula of the approach "standard" cannot derive a target titer if the internal control growth curve fails. Due to this there are no data points at the highest input copy number (1e9) and only two determinations, but quite off the real value, for the concentration 1e8.

At lower target concentrations (in the evaluation shown below 4e6) the standard quantification equation is used according to approach F1. Differentiation between the exceptional quantification formula F1 and the standard quantification formula is visible at target yields>4e6. Due to the failures of the internal control at concentrations 1e8 and 1e9 the exceptional quantification according to approaches F1 and F3 give superimposing results at these yields. Although quantification formula F1 is a very simple function and the assumption AF=2 is quite idealistic, this formula delivers excellent results for this set of data.

Quantification formula F2 according to approach "F2" with the amplification factor $AF = e^{b \ast \ln 10}$ overestimates the titer considerably. The amplification factor AF derived from the standard calibration curve appears to be not adequate (too high) for the high titer range. Accordingly, it might be appropriate to implement additional pre-checks to avoid an overestimation on basis of amplification factors derived from the calibration curve which are too high in view of the theoretical dynamics of the PCR amplification reaction. It might be appropriate to combine the amplification factor derived from the calibration curve with a predetermined theoretical amplification factor appropriately, for example by taking always the lower of the two amplification factors.

Approach "F3" on basis of exceptional quantification formula F1 and the condition of FIG. 19 give excellent results over the whole measurement range.

FIG. 23, as did FIG. 21, illustrates the deviation of the expected versus the found copy numbers on a log scale. The bars represent an assumed maximum deviation limit (±0.3 log). At low target titers the data points of the different functions are equal. Starting at 1e7 the functions separate from each other. At 1e8 only two values from the standard quantification approach appear which deviate substantially from the expected value. The presence of rectangles at log value "−3.0" come from all titer values which could not be determined due to failure of the internal control growth curves on basis of the standard quantification approach.

FIG. 24 shows schematically an example for the structure of a system, which can be used for implementing the invention. The system or quantification apparatus 100 has an amplification unit 102 which is adapted to perform PCR-amplification. In particular, a thermal cycler as known from EP 0 955 097 A1 can be included. Further, there is a detecting unit 104 for measuring fluorescent light emitted by sample-reagent mixtures amplified within amplification unit 102. Devices as known from EP 0 953 379 A1 and EP 0 953 837 A1 can be provided.

Both units 102 and 104 are controlled by a control unit 106, for example a work station on basis of an industry standard operating system and an industry standard micro processor. In particular, the control unit controls the amplification cycles effected by the amplification unit 102 and receives fluorescence intensity data from the detection unit 104. A control program defining the control processing and the data processing effected by the control unit 106 can be stored in a storage unit 108, e.g. a magnetic disc unit. Of course, there is also sufficient RAM memory. An input unit 110 is provided for inputting input data including (if desired) external calibration data into the system. The input unit can comprise a keyboard, a floppy disc drive or CD-ROM drive and a barcode reader, to give some examples. Further, there is an output unit 112, for example, comprising a display and a printer which serve in particular for outputting the quantification results.

In particular, for performing the method according to the invention a conventional Roche COBAS AmpliPrep™/COBAS TaqMan™ system as provided by Roche can be used, which, however, was adapted to perform the invention by providing control software which controls the system and interacts with the components of the system in such a way that the method of the invention is performed. In particular, the flow chart parts shown in FIGS. 18 and 19 and the alternate calibration formulas shown in FIGS. 17a and 17b can be implemented by the person skilled in the art without any problem in the control software of such a system using conventional programming techniques. Referring to FIGS. 1a, 1b, FIGS. 9, 10a, 10b and FIGS. 11a, 11b it should be remarked that these figures can be seen as diagrams indicating the data flow occurring in such a system and the control steps and data processing effected within such a system. On basis of the information contained herein the person skilled in the art is enabled to adapt a conventional quantification apparatus or the software thereof to perform the invention. Further, the person skilled in the art is enabled to provide software implementing the invention, which, when loaded in a conventional system, transforms the conventional system in a system embodying the invention.

Some specific embodiments of the invention referred to in the foregoing may be described as follows:

i) Quantification of Samples:

The samples are commonly amplified with an internal control by means of PCR.

Real time PCR is used (no end-point method).

The amplification products are detected by detection technology using two different fluorescent labels for the target and the internal control, e.g. in agreement with the detection formats and probes of the TaqMan™ instrument.

Threshold values or elbow values are determined on basis of the growth curves by defining a fixed threshold. The first, second or nth derivative of the growth curve is not used (however, this is possible in principle).

The fractional cycle numbers, at which the growth curve of the target and the growth curve of the internal control reach the threshold, are estimated.

From the difference between these fractional cycle numbers the initial titer of the target can be derived on basis of a predefined calibration formula or calibration curve.

ii) Providing the Calibration Formula or Calibration Curve:

A calibration panel with several dilution steps (a dilution series), which for example is adjusted on basis of the WHO-EUROHEP-Standard, is amplified on basis of several replica nucleic acids by means of state of the art PCR, e.g. in agreement with the detection formats and probes of the TaqMan™ instrument. The threshold cycles are determined. For each dilution stage (standard) the internal control is coprocessed in a fixed predetermined concentration.

The cycle differences between the target and the internal control which are determined for the respective standard are determined and evaluated on basis of a calibration function or formula. E.g., said cycle differences and the respective initial titer of the standards can be plotted in a diagram (cycle differences versus initial target titer).

An associated calibration curve or/and a calibration function can be generated which enable to calculate or determine the initial titer for arbitrary cycle differences which are measured.

iii) Quantification of Samples on Basis of a Bimodal or Multimodal Quantification Scheme:

The samples are commonly amplified with an internal control by means of PCR.

Real time PCR is used (no end-point method).

The amplification products are detected by detection technology using two different fluorescent labels for the target and the internal control, e.g. in agreement with the detection formats and probes of the TaqMan™ instrument.

Threshold values or elbow values are determined on basis of the growth curves by defining a fixed threshold. The first, second or n. derivative of the growth curve is not used (however, this is possible in principle).

The fractional cycle numbers, at which the growth curve of the target and the growth curve of the internal control reach the threshold, as estimated.

Depending on the situation, a standard quantification or an alternative (exceptional) quantification is selected. According to a first approach, an alternative quantification of the titer is selected, if the growth curve of the target reaches the threshold for a very early cycle, to evaluate the titer without reference to the cycle associated to the internal control. According to a second approach, there is the additional condition, that the alternative quantification formula is only selected, if the internal control concentration at the final stage of the amplification does not exceed a minimum plateau value. Generally, an alternative quantification of the target titer might be selected when the internal control drops out or is impaired due to competition, as can be expected for high target concentrations.

According to these approaches the alternative quantification of the internal control signal is sample-selectively not included in the calculation of the target titer for high target concentrations.

In other cases the initial target titer is evaluated on basis of the determined cycle differences using a predefined calibration curve or calibration formula (standard quantification).

iv) Providing Calibration Data for the Bimodal or Multimodal Quantification Scheme:

A calibration panel with several dilution steps (a dilution series), which for example is adjusted on basis of the WHO-EUROHEP-Standard, is amplified on basis of several replica nucleic acids by means of state of the art PCR, e.g. in agreement with the detection formats and probes of the TaqMan™ instrument. The threshold cycles are determined. For each dilution stage (standard) the internal control is coprocessed in a fixed predetermined concentration.

The cycle differences between the target and the internal control which are determined for the respective standard are determined and evaluated on basis of a calibration function or formula. E.G., said cycle differences and the respective initial titer of the standards can be plotted in a diagram (cycle differences versus initial target titer).

An associated calibration curve or/and a calibration function (generally calibration data) can be generated which enable to calculate or determine the initial titer for arbitrary cycle differences which are measured.

For the high titer range a second calibration curve or/and calibration function (generally calibration data) is generated on basis of the initial standard titer(s) (target) and the detected threshold cycle(s).

For arbitrary cycle differences measured or—in case of high initial target concentration—for arbitrary target threshold cycles the respective initial titer can be calculated or determined on basis of the calibration data (e.g. two calibration curves or formulas).

The above examples and experimental results show that it is possible to circumvent the problem of failure of the internal control at high titer concentrations of the target by providing at least two quantification schemes of different type, one of them using the characteristic value for the target nucleic acid as well as the characteristic value for the control nucleic acid and another using only the characteristic value for the target nucleic acid for the quantification. In particular, the invention provides a bimodal or multimodal titer calculation algorithm, for which alternative quantification approaches (e.g. quantification calibration formulas) might be used.

The benefits of the bimodal or multimodal quantification are in particular the following:

It is possible to determine titers with specified precision up to very high yields ($>10^{10}$ cps), which extends the dynamic range of conventional nucleic acid testing considerably.

High target concentrations have generally very solid and robust growth curves. The precision and recovery of these specimen would suffer considerably from the variance of less solid and less robust internal control growth curves. Thus, if the titer calculation for such high target considerations is done without internal control the quality of the quantification results can be improved (lower coefficient of variation (CV)).

Dropouts of the internal control signal which are caused by competition between the target and the internal control growth can appropriately dealt with. For practical applications, the dropout or generally the use of an "exceptional calibration formula" could be signaled to the user appropriately, so that the user is aware, that the internal control functionality of the internal control (IQS) was not evaluated (i.e. for high target concentrations when the internal control signal becomes very low or falls out completely).

It is not necessary to adjust the applied internal control copy number to higher values to enable an extended dynamic range to upper values of initial target titer. Instead it is possible to keep the internal control copy number low so that the competitional behavior does not effect the sensitivity of the assay.

For practical application the switching point between a high titer quantification function ("exceptional" calibration formula) and the standard evaluation (standard calibration formula) can be adjusted appropriately, depending on the desired dynamic range and the applied internal control copy number.

As far as a theoretical amplification factor is used, it might be appropriate to define the amplification factor test- or kitlot-specific. Compared to the theoretical value AF=2 used in foregoing, it might be appropriate to adjust the factor slightly to smaller values.

The use of a titer calculation formula without reference to the internal control for high initial titer values appears to be even more appropriate since the accuracy of a titer measurement scales inversely with the number of PCR cycles. Accordingly, at high target yields the error is smaller, because less cycles are involved in the quantification process. Accordingly, the internal control functionality of the internal control is less important.

The invention can be implemented in digital electronic circuitry, or in computer hardware, firmware, software, or in combinations of them. Apparatus of the invention can be implemented in a computer program product tangibly embodied in a machine readable storage device for execution by a programmable processor; and method steps of the invention can be performed by a programmable processor executing a program of instructions to perform functions of the invention by operating on input data and generating output.

The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high level procedural or object oriented programming language, or in assembly or machine language if desired; and in any case, the language can be a compiled or interpreted language. Suitable processors include, by way of example, both general and special purpose microprocessors. Generally, a processor will receive instructions and data from a read only memory and/or a random access memory. The essential elements of a computer are a processor for executing instructions and a memory.

Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. To provide for interaction with a user, the invention can be implemented on a computer system having a display device such as a monitor or LCD screen for displaying information to the user and a keyboard and a pointing device such as a mouse or a trackball by which the user can provide input to the computer system.

The invention was illustrated in the foregoing on basis of a number of exemplary embodiments and illustrative examples and measurement results. Other embodiments are possible. Accordingly, the invention shall only be limited by the contents and scope of the attached claims.

The invention claimed is:

1. A method for quantification of at least one target nucleic acid in a test sample, the method comprising:
   a) providing at least one target nucleic acid together with at least one internal control in a common test sample, said internal control comprising a defined initial amount ($Q_0$) of a control nucleic acid different from said target nucleic acid;
   b) amplifying said target nucleic acid and said control nucleic acid within said test sample in a common nucleic acid amplification process;
   c) measuring the amount of amplification product or a quantity indicating the amount of amplification product for said target nucleic acid and said control nucleic acid during said amplification in relation to an increasing progress parameter ($cycle_k$) representing the progress of said amplification process;
   d) determining a characteristic value ($nT_i$) of said progress parameter for said target nucleic acid on basis of measurement results related to the amount of amplification product for said target nucleic acid;
   e) if certain pre-defined conditions referring to the measured amount of amplification product for said control nucleic acid apply, determining a characteristic value ($nQ_i$) of said progress parameter for said control nucleic acid on basis of measurement results related to the amount of amplification product for said control nucleic acid, wherein said pre-defined conditions are selected from at least one of the following:
      i) the characteristic value for said control nucleic acid falls short of a predefined threshold value,
      ii) the characteristic value for said target nucleic acid exceeds a predefined threshold value,
      iii) the characteristic value for said control nucleic acid falls short of a threshold value defined in relation and greater than the characteristic value for said target nucleic acid,
      iv) the amount of amplification product or the quantity indicating the amount of amplification product for said control nucleic acid as measured or estimated for a final stage or near final stage of the amplification process exceeds of a predefined minimum plateau value,
      v) the amount of amplification product or the quantity indicating the amount of amplification product for said control nucleic acid as measured or estimated for a momentary state of the amplification process associated to the characteristic value for the target nucleic acid exceeds a predefined threshold value, the amount of amplification product, or the quantity indicating the amount of amplification product for said target nucleic acid as measured or estimated for said momentary state of the amplification process;
   f) selecting between a plurality of quantification schemes according to at least one predefined selection criterion, said selection being effected on basis of at least one of said measurement results related to the amount of amplification product for said target nucleic acid, measurement results related to the amount of amplification product for said control nucleic acid, and said characteristic value or values,
   wherein at least one quantification scheme of a first type provides for a quantification of the original amount ($T_{0i}$) of target nucleic acid in said test sample on basis of the characteristic value ($nT_i$) for said target nucleic acid, the characteristic value for said control nucleic acid ($nQ_i$) and associated reference data,
   wherein at least one quantification scheme of a second type provides for a quantification of the original amount ($T_{0i}$) of target nucleic acid in said test sample on basis of the characteristic value ($nT_i$) for said target nucleic acid and associated reference data without reference to any characteristic value ($nQ_i$) for said control nucleic acid; and
   g) quantifying the original amount of target nucleic acid ($T_{0i}$) in said test sample according to the selected quantification scheme on basis of at least the characteristic value ($nT_i$) determined for said target nucleic acid.

2. The method of claim 1, wherein selecting between a plurality of quantification schemes according to at least one predefined selection criterion includes selecting a quantification scheme of the second type if at least one of the following conditions applies:
   i) no characteristic value ($nQ_i$) for said control nucleic acid was determined,
   ii) the characteristic value for said control nucleic acid exceeds a predefined threshold value,
   iii) the characteristic value for said target nucleic acid ($nT_i$) falls short of a predefined threshold value,
   iv) the characteristic value for said control nucleic acid exceeds the characteristic value for said target nucleic acid by at least a predefined amount,
   v) the amount of amplification product or the quantity ($afi(n)$) indicating the amount of amplification product for said control nucleic acid as measured or estimated for a final stage or near final stage of the amplification process falls short of a predefined minimum plateau value ($afin_{ref}$),
   vi) the amount of amplification product or the quantity indicating the amount of amplification product for said control nucleic acid as measured or estimated for a momentary state of the amplification process associated to the characteristic value for the target nucleic acid falls short of a predefined threshold value or of the amount of amplification product or the quantity indicating the amount of amplification product for said target nucleic acid as measured or estimated for said momentary state of the amplification process.

3. The method according to claim 1, wherein said reference data associated to said quantification scheme of the first type are calibration data determined by
   A) providing at least one standard together with at least one internal control in a common sample, said standard comprising a defined initial amount ($T_{0i}$) of a standard nucleic acid, said internal control comprising a defined initial amount ($Q_0$) of a control nucleic acid, said standard nucleic acid and said control nucleic acid being different;
   B) amplifying said standard and said internal control within said sample in a common nucleic acid amplification process;

C) directly or indirectly measuring the amount of amplification product or a quantity indicating the amount of amplification product for said standard nucleic acid and said control nucleic acid during said amplification in relation to an increasing progress parameter (cycle$_k$) representing the progress of said amplification process;

D) determining a characteristic value (nT$_i$) of said progress parameter for said standard nucleic acid on basis of measurement results related to the amount of amplification product for said standard nucleic acid;

E) determining a characteristic value (nQ$_i$) of said progress parameter for said control nucleic acid on basis of measurement results related to the amount of amplification product for said control nucleic acid; and H) relating said initial amount of standard nucleic acid (T$_{0i}$) on the one hand and said characteristic values (nT$_i$, nQ$_i$) on the other hand with reference to said quantification scheme of the first type to provide said calibration data (a, b, c) associated to said quantification scheme of the first type.

4. The method according to claim 1, wherein said reference data associated to said quantification scheme of the second type are calibration data determined by:

AA) providing at least one standard in a sample, said standard comprising a defined initial amount of a standard nucleic acid;

BB) amplifying said standard in a nucleic acid amplification process;

CC) directly or indirectly measuring the amount of amplification product or a quantity indicating the amount of amplification product for said standard nucleic acid during said amplification in relation to an increasing progress parameter representing the progress of said amplification process;

DD) determining a characteristic value of said progress parameter for said standard nucleic acid on basis of measurement results related to the amount of amplification product for said standard nucleic acid; and HH) relating said initial amount (T$_{0i}$) of standard nucleic acid on the one hand and said characteristic value (nT$_i$) on the other hand with reference to said quantification scheme of the second type to provide said calibration data (A, B, C; T$_{ref}$, nT$_{ref}$) associated to said quantification scheme of the second type.

5. The method according to claim 4, wherein said reference data associated to said quantification scheme of the second type are calibration data determined or provided on basis of steps A) to D) and on basis of HH) relating said initial amount (T$_{0i}$) of standard nucleic acid on the one hand and said characteristic value (nT$_i$) associated to said standard nucleic acid on the other hand with reference to said quantification scheme of the second type to provide said calibration data (A, B, C; T$_{ref}$, nT$_{ref}$) associated to said quantification scheme of the second type.

6. The method according to claim 3, wherein said standard is an external standard, said sample being different from said test sample.

7. The method according to claim 3, wherein said defined initial amount (Q$_i$) of said control nucleic acid being amplified together with said standard nucleic acid is the same as said defined initial amount (Q$_0$) of said control nucleic acid being amplified together with said target nucleic acid.

8. The method according to claim 3, wherein said standard nucleic acid corresponds to said target nucleic acid.

9. The method according to claim 3, wherein said calibration data (a, b, c) associated to said quantification scheme of the first type or said calibration data (A, B, C; T$_{ref}$, nT$_{ref}$) associated to said quantification scheme of the second type are provided together with constituents of a quantification kit.

10. The method according to claim 3, wherein in step A) a dilution series (T$_{0i}$ (i=1, ..., S)) of said standard nucleic acid is provided, each dilution within a respective sample together with said internal control, wherein steps B) to E) are effected with respect to all samples of said dilution series, and wherein step H) comprises:

relating the initial amounts (T$_{0i}$) of standard nucleic acid of said samples and the characteristic values (nT$_i$, nQ$_i$) determined for said samples with reference to said quantification scheme of the first type to provide said calibration data (a, b, c) associated to said quantification scheme of the first type.

11. The method according to claim 10, wherein said reference data associated to said quantification scheme of the second type are calibration data determined on basis of steps A) to D) and on basis of HH) relating the initial amount (T$_{0j}$) of standard nucleic acid of a selected or predefined one of said samples and the characteristic value (nT$_j$) associated to said standard nucleic acid determined for said sample being selected with reference to said quantification scheme of the second type to provide said calibration data (T$_{ref}$, nT$_{ref}$) associated to said quantification scheme of the second type.

12. The method according to claim 11, wherein said reference data associated to said quantification scheme of the second type are calibration data determined or provided on basis of steps A) to D) and on basis of HH) relating the initial amounts (T$_{0i}$) of standard nucleic acid of said samples and the characteristic values (nT$_i$) associated to said standard nucleic acid determined for said samples with reference to said quantification scheme of the second type to provide said calibration data (A, B, C) associated to said quantification scheme of the second type.

13. The method according to claim 4, wherein in step AA) only one sample including a selected defined initial amount (T$_{0j}$) of said standard nucleic acid is provided.

14. The method according to claim 4, wherein in step AA) a dilution series (T$_{0i}$ (i=1, ..., S)) of said standard nucleic acid is provided, each dilution being within a respective sample, wherein steps BB) to DD) are effected with respect to all samples of said dilution series, and wherein step HH) comprises:

relating the initial amounts (T$_{0i}$) of standard nucleic of said samples and the characteristic values (nT$_i$) determined for said samples with reference to said quantification scheme of the second type to provide said calibration data (A, B, C) associated to said quantification scheme of the second type.

15. The method according to claim 9, wherein the calibration data associated to said quantification scheme of the second type include a fixed amplification efficiency ($\epsilon$) or wherein in step g) the calibration data associated to said quantification scheme of the second type are used together with a fixed amplification efficiency ($\epsilon$) for the quantification of the original amount of target nucleic in said test sample according to the quantification scheme of the second type.

16. The method according to claim 15, wherein a theoretical amplification efficiency ($\epsilon$) of said amplification process is used as said fixed amplification efficiency.

17. The method according to claim 1, wherein said amplification process is effected in cycles and a cycle number indicating the number of elapsed cycles is used as progress parameter.

18. The method according to claim 1, wherein at least one of step d) and step e) comprises:
deriving a growth curve from the respective measurement results,
identifying a characteristic of the respective growth curve or of a derivative calculated of the respective growth curve, and
determining the characteristic value ($nT_i$; $nQ_i$) associated with said characteristic.

19. The method according to claim 18, wherein the characteristic of the respective growth curve corresponds to a crossing of a threshold by the growth curve, said threshold being predefined to represent an unnormalized growth value or being determined on basis of respective measurement results to represent a normalized growth value.

20. The method according to claim 1, wherein according to said quantification scheme of the first type a secondary characteristic value ($\Delta n_i$) is determined from said characteristic value ($nT_i$) for said target nucleic acid or standard nucleic acid, respectively, and said characteristic value ($nQ_i$) of said control nucleic acid, said secondary characteristic value representing a direct or indirect measure of at least one of the amplification and the original amount ($T_{0i}$) of said target nucleic acid or initial amount ($T_{0i}$) of said standard nucleic acid, respectively, relative to at least one of the amplification and the defined initial amount ($Q_0$) of said control nucleic acid, and wherein the original amount ($T_{0i}$) of target nucleic acid is quantified on basis of said secondary characteristic value ($\Delta n_i$) and said reference data (a, b, c) associated thereto.

21. The method according to claim 20, wherein step H) comprises:
relating said initial amount ($T_{0i}$) of standard nucleic acid and said secondary characteristic value ($\Delta n_i$) with reference to said quantification scheme of the first type to provide said calibration data (a, b, c) associated to said quantification scheme of the first type.

22. The method according to claim 1, wherein according to said quantification scheme of the first type a difference value ($\Delta n_i$) representing the difference between the characteristic value ($nT_i$) for said target nucleic acid or standard nucleic acid, respectively, and the characteristic value ($nQ_i$) of said control nucleic acid is determined, and wherein the original amount ($T_{0i}$) of target nucleic acid is quantified on basis of said difference value ($\Delta n_i$) and said reference data (a, b, c) associated thereto.

23. The method according to claim 22, wherein step H) comprises:
relating said initial amount of standard nucleic acid and said difference value with reference to said quantification scheme of the first type to provide said calibration data associated to said quantification scheme of the first type.

24. The method according to claim 1, wherein said amplification process comprises a polymerase chain reaction (PCR) process or wherein said amplification process comprises or is part of a reverse transcriptase polymerase chain reaction (RT-PCR) process.

25. The method according to claim 24, wherein in said amplification process said target nucleic acid or standard nucleic acid and said control nucleic acid are competitively amplified on basis of the same primers for the target nucleic acid or standard nucleic acid and for said control nucleic acid.

26. The method according to claim 1, wherein selecting between a plurality of quantification schemes includes selecting between a quantification of said target nucleic acid in said test sample and a determination of presence or non-presence of said target nucleic acid in said test sample, and if selected, determining the presence or non-presence of said target nucleic acid in said test sample on the basis of measurement results obtained in step c).

27. Apparatus for quantification of at least one target nucleic acid in a test sample or in a plurality of test samples, the apparatus comprising:
an amplification unit for effecting a nucleic acid amplification process with respect to at least one test sample;
a detection unit for measuring, at a plurality of different times during said nucleic acid amplification process effected by said amplification unit, at least two signals being related to a respective nucleic acid which is amplified in the amplification process, the detection mechanism being adapted to independently measure at least one first signal related only to a first nucleic acid and at least one second signal related only to a second nucleic acid or to measure at least one first signal and at least one second signal from which first data related only to a first nucleic acid and second data related only to a second nucleic can be calculated;
a controller in communication with said amplification unit and said detection mechanism;
wherein said controller is configured to perform operations comprising:
bb) controlling the amplification unit to effect an amplification with respect to at least one respective test sample;
cc) controlling the detection unit to directly or indirectly measure the amount of amplification product or a quantity indicating the amount of amplification product for at least two different nucleic acids, namely with respect to at least one first nucleic acid and with respect to at least one second nucleic acid;
dd) determining a characteristic value ($nT_i$) of said progress parameter for said first nucleic acid on basis of measurement results related to the amount of amplification product for said first nucleic acid;
ee) if certain pre-defined conditions referring to the measured amount of amplification product for said second nucleic acid apply, determining a characteristic value ($nQ_i$) of said progress parameter also for said second nucleic acid on basis of measurement results related to the amount of amplification product for said second nucleic acid, wherein said pre-defined conditions are selected from at least one of the following:
i) the characteristic value for said second nucleic acid falls short of a predefined threshold value,
ii) the characteristic value for said first nucleic acid exceeds a predefined threshold value,
iii) the characteristic value for said second nucleic acid falls short of a threshold value defined in relation and greater than the characteristic value for said first nucleic acid,
iv) the amount of amplification product or the quantity indicating the amount of amplification product for said second nucleic acid as measured or estimated for a final stage or near final stage of the amplification process exceeds of a predefined minimum plateau value,
v) the amount of amplification product or the quantity indicating the amount of amplification product for said second nucleic acid as measured or estimated for a momentary state of the amplification process associated to the characteristic value for the first nucleic acid exceeds a predefined threshold value, the amount of amplification product, or the quantity indicating the amount of amplification product for said first nucleic acid as measured or estimated for said momentary state of the amplification process;

ff) selecting between a plurality of quantification schemes according to at least one predefined selection criterion, said selection being effected directly or indirectly on basis of at least one of said measurement results related to the amount of amplification product for said first nucleic acid, measurement results related to the amount of amplification product for said second nucleic acid and said characteristic value or values, wherein at least one quantification scheme of a first type provides for a quantification of the original amount ($T_{0i}$) of first nucleic acid in said test sample on basis of the characteristic value ($nT_i$) for said first nucleic acid, the characteristic value ($nQ_i$) for said second nucleic acid and associated reference data, wherein at least one quantification scheme of a second type provides for a quantification of the original amount ($T_{0i}$) of first nucleic acid in said test sample on basis of the characteristic value ($nT_i$) for said first nucleic acid and associated reference data without reference to any characteristic value ($nQ_i$) for said second nucleic acid, gg) quantification of the original amount ($T_{0i}$) of first nucleic acid in said test sample according to the selected quantification scheme on basis of at least the characteristic value ($nT_i$) determined for said first nucleic acid, jj) providing quantification data which include said original amount ($T_{0i}$) of first nucleic acid to represent the original amount ($T_{0i}$) of target nucleic in said test sample.

28. A computer program product, embodied in tangible medium, the product comprising instructions executable by an apparatus for quantification of at least one target nucleic acid in a test sample or in a plurality of test samples, the apparatus comprising:

an amplification unit for effecting a nucleic acid amplification process with respect to at least one test sample;

a detection mechanism for measuring, at a plurality of different times during said nucleic acid amplification process effected by said amplification unit, at least two signals being related to a respective nucleic acid which is amplified in the amplification process, the detection mechanism being adapted to independently measure at least one first signal related only to a first nucleic acid and at least one second signal related only to a second nucleic acid or to measure at least one first signal and at least one second signal from which first data related only to a first nucleic acid and second data related only to a second nucleic can be calculated;

a controller in communication with said amplification unit and said detection mechanism;

wherein said controller in response to said instructions performs operations comprising:

bb) controlling the amplification unit to effect an amplification with respect to at least one respective test sample;

cc) controlling the detection unit to directly or indirectly measure the amount of amplification product or a quantity indicating the amount of amplification product for at least two different nucleic acids, namely with respect to at least one first nucleic acid and with respect to at least one second nucleic acid;

dd) determining a characteristic value ($nT_i$) of said progress parameter for said first nucleic acid on basis of measurement results related to the amount of amplification product for said first nucleic acid;

ee) if certain pre-defined conditions referring to the measured amount of amplification product for said second nucleic acid apply, determining a characteristic value ($nQ_i$) of said progress parameter also for said second nucleic acid on basis of measurement results related to the amount of amplification product for said second nucleic acid, wherein said pre-defined conditions are selected from at least one of the following:

i) the characteristic value for said second nucleic acid falls short of a predefined threshold value, ii) the characteristic value for said first nucleic acid exceeds a predefined threshold value, iii) the characteristic value for said second nucleic acid falls short of a threshold value defined in relation and greater than the characteristic value for said first nucleic acid, iv) the amount of amplification product or the quantity indicating the amount of amplification product for said second nucleic acid as measured or estimated for a final stage or near final stage of the amplification process exceeds of a predefined minimum plateau value, v) the amount of amplification product or the quantity indicating the amount of amplification product for said second nucleic acid as measured or estimated for a momentary state of the amplification process associated to the characteristic value for the first nucleic acid exceeds a predefined threshold value, the amount of amplification product, or the quantity indicating the amount of amplification product for said first nucleic acid as measured or estimated for said momentary state of the amplification process;

ff) selecting between a plurality of quantification schemes according to at least one predefined selection criterion, said selection being effected directly or indirectly on basis of at least one of said measurement results related to the amount of amplification product for said first nucleic acid, measurement results related to the amount of amplification product for said second nucleic acid and said characteristic value or values, wherein at least one quantification scheme of a first type provides for a quantification of the original amount ($T_{0i}$) of first nucleic acid in said test sample on basis of the characteristic value ($nT_i$) for said first nucleic acid, the characteristic value ($nQ_i$) for said second nucleic acid and associated reference data, wherein at least one quantification scheme of a second type provides for a quantification of the original amount ($T_{0i}$) of first nucleic acid in said test sample on basis of the characteristic value ($nT_i$) for said first nucleic acid and associated reference data without reference to any characteristic value ($nQ_i$) for said second nucleic acid, gg) quantification of the original amount ($T_{0i}$) of first nucleic acid in said test sample according to the selected quantification scheme on basis of at least the characteristic value ($nT_i$) determined for said first nucleic acid, jj) providing quantification data which include said original amount ($T_{0i}$) of first nucleic acid to represent the original amount ($T_{0i}$) of target nucleic in said test sample.

29. A server computer system storing the computer program product according to claim 28 for downloading via a communication link.

* * * * *